(12) United States Patent
Verenchikov

(10) Patent No.: US 9,683,963 B2
(45) Date of Patent: Jun. 20, 2017

(54) ION MOBILITY SPECTROMETER WITH HIGH THROUGHPUT

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 23 days.

(21) Appl. No.: 14/418,856

(22) PCT Filed: May 2, 2013

(86) PCT No.: PCT/US2013/039328
§ 371 (c)(1),
(2) Date: Jan. 30, 2015

(87) PCT Pub. No.: WO2014/021960
PCT Pub. Date: Feb. 6, 2014

(65) Prior Publication Data
US 2015/0233866 A1    Aug. 20, 2015

Related U.S. Application Data

(60) Provisional application No. 61/677,881, filed on Jul. 31, 2012.

(51) Int. Cl.
*H01J 49/00* (2006.01)
*G01N 27/62* (2006.01)
(Continued)

(52) U.S. Cl.
CPC .......... *G01N 27/622* (2013.01); *H01J 49/061* (2013.01); *H01J 49/40* (2013.01)

(58) Field of Classification Search
None
See application file for complete search history.

(56) References Cited

U.S. PATENT DOCUMENTS 5,521,379 A * 5/1996 Franzen ................ B01J 19/087
250/282
6,291,821 B1 * 9/2001 Danylewych-May G01N 27/622
250/286
(Continued)

FOREIGN PATENT DOCUMENTS

CN    101632148 A    1/2010
CN    104067116 A    9/2014
(Continued)

OTHER PUBLICATIONS

International Search Report dated Oct. 1, 2013, relating to International Application No. PCT/US2013/039328.
(Continued)

*Primary Examiner* — Andrew Smyth
(74) *Attorney, Agent, or Firm* — Honigman Miller Schwartz and Cohn LLP

(57) ABSTRACT

A method and apparatus are disclosed for improving ion mobility spectrometry by using a fast and spatially wide ion gate based on local RF field barrier opposed to a switching DC field. Alternatively, the speed and charge throughput of ion mobility separator are improved by arranging coaxial mobility cell followed by conical coaxial ion channel. The improvement accelerates the ion mobility analysis and improves charge throughput and dynamic range of the IMS. The invention is particularly suited for rapid dual gas chromatography, fast CE. Preferably, the accelerated and wide bore IMS is coupled to a multi-reflecting time-of-flight mass spectrometer with a fast encoded orthogonal acceleration. Speed and sensitivity of IMS with fast pulsing MR-
(Continued)

TOF make it practical to arrange analytical methods of comprehensive and orthogonal separation in multiple analytical dimensions.

22 Claims, 13 Drawing Sheets

(51) Int. Cl.
*H01J 49/06* (2006.01)
*H01J 49/40* (2006.01)

(56) References Cited

U.S. PATENT DOCUMENTS

| | | | |
|---|---|---|---|
| 7,170,053 B2 | 1/2007 | Shvartsburg et al. | |
| 7,772,564 B2* | 8/2010 | Kruit | H01J 27/205 250/423 R |
| 7,838,823 B1* | 11/2010 | Pfeifer | G01N 27/622 250/281 |
| 2001/0032930 A1* | 10/2001 | Gillig | H01J 49/06 250/288 |
| 2003/0132379 A1 | 7/2003 | Li | |
| 2004/0046124 A1* | 3/2004 | Derrick | H01J 49/065 250/396 R |
| 2005/0205775 A1* | 9/2005 | Bromberg | H01J 49/0031 250/290 |
| 2005/0230634 A1* | 10/2005 | Bajic | H01J 49/044 250/423 R |
| 2005/0269518 A1* | 12/2005 | Bajic | H01J 49/044 250/423 F |
| 2006/0231751 A1* | 10/2006 | Zuleta | H01J 49/0018 250/287 |
| 2006/0284076 A1* | 12/2006 | Scheidemann | H01J 49/105 250/288 |
| 2007/0158545 A1* | 7/2007 | Verentchikov | H01J 49/004 250/282 |
| 2007/0187591 A1* | 8/2007 | Bromberg | H01J 49/40 250/290 |
| 2008/0142700 A1* | 6/2008 | Dahl | G01N 27/622 250/286 |
| 2008/0156978 A1 | 7/2008 | Shvartsburg et al. | |
| 2008/0179515 A1 | 7/2008 | Sperline | |
| 2009/0108194 A1 | 4/2009 | Page et al. | |
| 2009/0134321 A1* | 5/2009 | Hoyes | C08L 23/04 250/282 |
| 2009/0173880 A1* | 7/2009 | Bateman | H01J 49/065 250/292 |
| 2009/0256070 A1* | 10/2009 | Nagano | H01J 49/4245 250/282 |
| 2009/0294644 A1* | 12/2009 | Belov | G01N 27/622 250/282 |
| 2009/0294662 A1* | 12/2009 | Belov | H01J 49/066 250/291 |
| 2010/0038530 A1* | 2/2010 | Giles | H01J 49/4275 250/283 |
| 2010/0044561 A1 | 2/2010 | Giles | |
| 2010/0193679 A1* | 8/2010 | Nikolaev | H01J 37/248 250/282 |
| 2011/0189788 A1* | 8/2011 | Brown | H01J 49/0072 436/173 |
| 2011/0210242 A1* | 9/2011 | Bateman | H01J 27/02 250/282 |
| 2012/0326020 A1* | 12/2012 | Ivashin | G01N 27/622 250/282 |
| 2013/0048852 A1* | 2/2013 | Verenchikov | H01J 49/0031 250/282 |
| 2013/0236362 A1* | 9/2013 | Li | H01J 27/024 422/83 |

FOREIGN PATENT DOCUMENTS

| | | | | |
|---|---|---|---|---|
| EP | 2455963 | A2 | 5/2012 | |
| GB | 2390935 | A | 1/2004 | |
| GB | 2413433 | A * | 10/2005 | G01N 27/624 |
| GB | 2413433 | A | 10/2005 | |
| GB | 2413433 | B * | 3/2007 | G01N 27/624 |
| GB | 2478300 | A | 9/2011 | |
| GB | 2486584 | A | 6/2012 | |
| WO | WO-9808087 | A1 | 2/1998 | |
| WO | WO-2008103492 | A2 | 8/2008 | |
| WO | WO-2011135477 | A1 | 11/2011 | |
| WO | WO 2012021124 | A1 * | 2/2012 | G01N 27/624 |
| WO | WO-2013067366 | A2 | 5/2013 | |

OTHER PUBLICATIONS

Chinese Office Action for Application No. 201380040768.5 dated Nov. 28, 2016 with English translation thereof.

* cited by examiner

US 9,683,963 B2

ION MOBILITY SPECTROMETER WITH HIGH THROUGHPUT

TECHNICAL FIELD

This disclosure relates to the area of ion mobility spectrometry, and more in particular related to improving ion mobility spectrometry for coupling with liquid and gas chromatography, multidimensional gas chromatography, and with mass spectrometry.

BACKGROUND

Ion mobility spectrometers (IMS) are widely used for analyzing ionized compounds by their mobility, which is the function of ion charge, mass and shape. Typical IMS comprises an ion source for soft ionization of analyte compounds, an ion gate (typically Tyndal gate) to form short ion packets, a gas filled drift tube for ion separation in electrostatic fields, and a collector to measure time dependent signal. As a standalone analytical technique, IMS has a generally low resolution (substantially at or between 50-100). IMS has been primarily considered as a low cost hand-held system and method for detecting toxic volatile compounds, as it has a generally low detection limit that can be enhanced by utilizing specific ion molecular reactions with doping vapors. More recently IMS has been coupled with gas chromatography (GC), liquid chromatography (LC) and mass spectrometry (MS), where IMS brings an additional dimension of analytical separation. However, the straight forward coupling can yield strong signal losses in IMS due to at or about ~1% duty cycle of a Tyndal ion gate and a mismatch in gas pressures and ion cloud size between IMS and MS. In addition, employing scanning MS (e.g., quadrupoles and the like) there is a mismatch in time scales.

U.S. Pat. No. 5,200,614, incorporated herein by reference in its entirety, discloses an improvement to IMS sensitivity by trapping ions between gate pulses. U.S. Pat. No. 3,902,064, incorporated herein by reference in its entirety, discloses a combination using an IMS spectrometer with a downstream mass spectrometer for complimenting mobility measurements by ion mass measurements. Young et al., in paper J. Chem. Phys., v. 53, No 11, pp. 4295-4302, incorporated herein by reference in its entirety, discloses a combination using an IMS spectrometer with a downstream orthogonally accelerating time-of-flight detector that is generally capable for fast recordation of panoramic (all mass) spectra for higher speed and duty cycle of mass measurements. U.S. Pat. No. 5,905,258, incorporated herein by reference in its entirety, discloses a combination of both features—an ion trap in-front of the IMS and an orthogonal TOF past IMS, thus capitalizing on both advantages—higher duty cycle of IMS and MS.

U.S. Pat. No. 6,107,628, incorporated herein by reference in its entirety, discloses an ion funnel device for converging ion flows at intermediate gas pressures. U.S. Pat. No. 6,818,890, incorporated herein by reference in its entirety, discloses an ion funnel for ion confinement past IMS. Paper Anal. Chem., 2008, v. 80, pp. 612-623, incorporated herein by reference in its entirety, describes using an ion funnel device for both—for ion trapping prior to IMS and for ion confinement beyond the IMS. Details on the so-called hourglass ion funnel trap are also presented in Anal. Chem., 2007, v. 79, pp. 7845-7852, incorporated herein by reference in its entirety. The described method presents the ultimately sensitive IMS-MS from the prior art, which still generally suffers several limitations. The number of trapped ions is limited by the space charge capacity of the ion trap and of IMS drift tube to at or about 1E+7 charges per pulse which is normally accumulated in at or around 1 ms time. Both—the hourglass gate and downstream ion funnel do spread ion packets to substantially at or between about (200-400) µs, which slows down the IMS speed, requires long drift separation time of substantially at or between about (20-40) ms, requires constructing long (about 1 m long) IMS drift tubes, and limits the IMS duty cycle (at or about 1 ms of gate saturation vs. at or about 40 ms cycle), charge throughput, and the dynamic range.

WO2008112351, incorporated herein by reference in its entirety, discloses a method of improving IMS dynamic range and space charge capacity by multiplexed coding of the ion trap which operates at much higher net frequency compared to conventional regime of single trap firing per IMS separation. However, the approach can cause ion packets overlapping and confusions at data interpretation. In order to match IMS separation time the employed downstream orthogonal TOF has at or about 100 µs pulse period and hence has limited resolution (at or about R=5,000).

Summarizing the above, IMS and IMS-TOF of prior art are limited in their charge throughput, dynamic range, speed, and resolution, which limits their combination with fast separation methods. Therefore, improving IMS and IMS-TOF parameters is beneficial as described herein.

SUMMARY

The inventor has realized that the charge throughput and the speed of IMS can be increased as compared against the prior art devices and method by forming much shorter, spatially uniform and wider ion packets at IMS gate. The inventor proposes a novel trapping gate comprising a dual mesh with an RF signal applied between meshes, thus forming an RF barrier for accumulating ions at gas pressures from substantially at or between about (1 to 100) mBar. In an implementation, ions can be either pulsed ejected to form substantially at or between about (10-20) µs packets, or released in a mass-dependent fashion, e.g., by a ramped DC field. Formation of short ion packets potentially allows shortening the IMS spectrometer in size and obtaining an order of magnitude faster speed (substantially at or between (1-2) ms cycles), higher throughput, and dynamic range—all generally important for the use with rapid upfront separating devices, like GC×GC or LC×CE separation, for rapid surface analysis, and for tracking rapid in-source reactions.

To match the gate speed, preferably a shorter (substantially at or between about (10-20) cm) An IMS drift tube may be used in combination with a higher gas pressure of substantially at or between about (10-100) Torr. A fine cell grid (substantially at or between about (0.1-1) mm) is expected to provide an RF barrier at such elevated pressures. In an implementation, ions (entrained into a gas jet) are introduced from a side of the gate, such that ions would be passing above the gate. The arrangement can generally eliminate any carry-over between ejection cycles and generally allows removing light ions, which are generally of no analytical interest and likely to carry most of the current.

An alternative solution for space charge throughput is proposed, wherein IMS is arranged between coaxial cylinders with at least one RF repelling wall. The cylindrical IMS is then coupled by conical converging ion guide. The inventor realized that RF excitation cause a delay in ion propagation time, contrary to current opinion that RF excitation drops IMS resolution. Because of low time spread past the IMS compared to ion funnels, the arrangement generally allows rapid IMS cycling thereby enhancing the charge throughput.

In a group of embodiments, according to an implementation, the IMS may be preceded either by a fast separating chromatography, like dual GC, or by a second slower separating IMS, optionally with a fragmentation cell in-between, or by an ion source which generates rapid changes in ion composition, like sources for rapid surface scanning, or ion sources generating chemical or ion molecular reactions at time scale down to milliseconds. Fast IMS-TOF cycling becomes possible due to rapid pulsing of the downstream MR-TOF MS.

In a group of embodiments, according to an implementation, the IMS is followed by a multi-reflecting (MR) TOF MS, equipped with encoded fast pulsing of the orthogonal accelerator (OA). Average pulsing rates are chosen sufficient to record time profiles of upfront separation stages. The chromatographic profiles, IMS profiles, and MR-TOF flight times are decoded based on information on uneven pulse intervals while analyzing intensity distributions within encoded signal series. Such mass spectrometers are generally capable of tracking input changes down to substantially at or between about (5-10) µs time scale. To increase charge throughput, the IMS triggering may be accelerated, while still generally avoiding time overlaps between ions of the same mass to charge (m/z). In an implementation, to support the speed of IMS separation and to generally reduce ion packet time spread, the IMS exit section may be equipped with either an ion funnel having a central section, or by converging multipole built as a stack of printed circuit boards, preferably followed by a conductive ion guide with axial field gradient. In a group of embodiments, according to an implementation, the IMS separation space is formed between coaxial cylinders with at least one cylinder forming an RF surface for ion radial repulsion. Formation of ring shaped ion packets can generally allow the use of conical RF ion funnels or RF conical guides to confine the packets radially without additional time spreads that are generally typical for wide open ion funnels.

In an implementation, optionally, a mass dependent gate located after a single mirror reflection allows the substantial simultaneous admission onto an MR-TOF detector of ions with correlated m/z and mobility for the purpose of selecting charge states or compound classes. The fast encoded pulsing improves spectrometer sensitivity and provides rapid tracking of both—GC2 and IMS profiles. IMS separation improves spectral decoding step and accurate mass measurements in MR-TOF. IMS time serves as an additional dimension for high throughput identification based on 3-D coordinate tag of retention time, mobility, and accurate mass. Rapid operation of IMS with frequent pulsing MR-TOF provides multiple advantages and allows implementing multiple novel operation regimes and analytical approaches described below. Fast and sensitive IMS-MR-TOF tandem makes practical multi-dimensional separation in realistic analysis time. Introduction of novel features—rapid IMS gate and introduction of imbedded fast encoded and uneven pulse strings for IMS and MR-TOF—can yield a novel opportunity of comprehensive and non-compromised multi-dimensional analyses, such as GC×GC-IMS-MRTOF or pseudo MS-MS at chromatographic time scale and ultra-high resolution and sub-ppm mass accuracy of MR-TOF MS.

In one group of embodiments, according to an implementation, a fragmentation cell may be used to fragment IMS-separated parent ions to thereby provide all-mass pseudo-MS-MS (i.e., simultaneous tandem MS analysis for all parent ions and without ion losses at parent ion selection.) In an implementation, fragments may be gathered into families by deconvolution of their time profiles with the account of calibrated mass dependent delay in the CID cell. Parent masses may be recovered by observation of molecular peak in fragment spectra. In an implementation, deconvolution of time profiles for parent ions is expected to improve parent ion separation to at or between about 200-300 resolution which is generally comparable to MS1 resolution in conventional MS-MS experiments. In some embodiments, the CID cell used for soft fragmentation in order to fragment mobility selected clusters of chemical background.

In another group of embodiments, according to an embodiment, the tandem of IMS with frequent pulsing MR-TOF is proposed for measurements of differential ion mobility, first time without so-called scanning ion losses. Accurate mass measurements allow tracking mobility of individual compounds. In an implementation, field strength is varied multiple times to derive the difference in ion mobility and data are preferably displayed in the analytical space of ion mobility and differential ion mobility. Preferably, light gases are used for reaching significant changes in the mobility without ion fragmentation. Preferably, the IMS length is extended and folded as described below.

In an implementation, there is provided a fast ion mobility spectrometer (IMS) matching high speed of GC×GC analysis with at or about 50 ms wide peaks. Said fast IMS sequentially comprises: an ion source, said source being filled with gas at gas pressure from substantially at or between 1 mBar to 1 Bar; an ion gate formed of a front cap electrode, followed by a front mesh and then by a back mesh; said meshes are parallel and spaced at a distance comparable to mesh cell size; a radiofrequency (RF) generator connected between said meshes; a switching or adjustable DC signal connected to said cap electrode and said meshes; an ion drift space filled with gas at pressure from substantially at or between about (1 to 100) mBar; and an ion detector.

In an implementation, the dual RF mesh gate can save IMS duty cycle and generate short ion packets (at or about 10 µs), this way improving IMS speed, charge throughput and dynamic range. Preferably, the axis of said ion source may be oriented substantially parallel to said meshes. Preferably, the apparatus may further comprise at least one RF ion guide between said ion source and said ion gate, and wherein said RF ion guide comprise one of the group: (i) an ion funnel; (ii) a multipole ion guide with axial field. Preferably, the apparatus may further comprise either an upfront liquid chromatograph, or capillary electrophoresis, or gas chromatograph, or dual stage gas chromatograph. Preferably, said ion source may comprise one of the group: (i) ESI, APCI (i) a photoionization source; (ii) a photochemical ionization source with a dopant; (iii) a chemical ionization source with proton transfer reactions; (iv) a chemical ionization source with electron attachment ionization; (v) a glow discharge source with analyte ionization by conditioned products of glow discharge. Preferably, said source may have means for switching between ionization modes or for switching between ion polarities. Preferably, said source may have fragmentation means and means for switching said fragmentation at time scale of chromatographic separation. To improve speed of the ion detector, ions packets may be confined spatially, either by increased electrostatic field or by radio frequency ion funnels.

Formation of pancake shaped and large diameter (substantially at or between about (50-200) mm) ion clouds reduces effects of space charge onto the IMS performance. Minimal packet width (substantially at or between about (10-100)μs) allows frequent operation of the IMS. Both means can improve space charge throughput and operation speed of the IMS. To avoid distortion of ion gating by gas flows, the ion source is oriented along the gate, and/or an ion guide is employed to deliver ions to a remote located ion gate.

In an implementation, there is provided an ion mobility spectrometer comprising: (a) two coaxial set of electrodes, outer and inner; (b) within each of said sets, said electrodes are connected via resistive chain for providing axial DC gradient; (c) within at least one set of electrodes, said electrodes are connected to alternated radio-frequency supply for radial ion repulsion; and (d) DC potential distribution between two sets is biased such that to provide radial DC field, pushing ions against said RF barrier. Preferably, the apparatus further comprises at least one ion transfer device of the least: (i) a coaxial radiofrequency ion guide; (ii) a coaxial radiofrequency ion trap upfront of said mobility spectrometer; (iii) a conical ion guide or an ion funnel with axial DC field; and (iv) a conical coaxial ion guide with axial DC field, having inner conical set of electrodes for providing radial DC repulsion; said devices being located either upstream or downstream of said mobility spectrometer.

The embodiments capitalize on the novel realization—RF excitation does not affect IMS resolution, but rather causes a time delay. RF fields can be used for radial ion confinement if providing either effective ion mixing between regions of low and high RF amplitude, or by soft pushing of ions onto an RF barrier, such that they all experience about the same time delay. Ion confinement into ring packets allows avoiding time spread typical for prior art wide open ion funnels, this way enhancing IMS resolution and operational speed. Note, that the coaxial IMS may employ either RF mesh gate or other coaxial ion traps, like RF ion tunnels and funnels, ring RF trap with radial ejection and an array of multipoles with edge pulse ejection.

In another implementation, there is provided an ion mobility spectrometer comprising an array of radiofrequency ion guides with distributed axial DC field, said array being spatially arranged either as a two dimensional planar array, or coaxially wrapped two dimensional array, or a three-dimensional array comprising multiple planar layers. Preferably, said array comprises printed circuit boards with conductive segments, said segments being either separated by deep slot or by antistatic material. The array of ion channels may be used in parallel for improving IMS charge throughput, or sequentially for increasing length and resolution of the IMS.

In another implementation, there is provided a method of rapid ion mobility spectrometric analysis, sequentially comprising the following steps: generating ions within an ion source operating at gas pressure from at or between about 1 mBar to 1 Bar; forming a local RF field between closely spaced parallel meshes while attracting ions toward the RF field region by a DC field which is sufficiently small to prevent ion penetration through the barrier of said RF field and this way causing ion localization in local RF traps around mesh cells; propelling ions through said RF field by a pulsed switch of a DC field in the region of said RF field, thus forming short ion packets; separating ions by their mobility within an electrostatic field at gas pressure from at or between about (1 to 100) mBar; and detecting a time dependent signal on a detector.

Preferably, ions may be introduced into the RF field region substantially parallel to said mesh plane. Preferably, the method may further comprise a step of ion transfer between said ionization and said gating steps; said transfer step is assisted by radiofrequency confinement of ions in order to adopt a difference between gas pressures and to avoid significant gas motion within the mobility separation stage. Preferably, the method may further comprise a step of analyte separation either by a method of gas chromatographic separation or by a method of dual stage gas chromatographic separation, liquid chromatography or electrophoresis. Preferably, said ionization step may comprise one step of the group: a photoionization; a photo-chemical ionization with a dopant; a chemical ionization with proton transfer reactions; a chemical ionization with electron attachment ionization; analyte ionization by conditioned products of a glow discharge, an electrospray ionization; an atmospheric pressure photo-chemical ionization; an atmospheric pressure chemical ionization; and matrix assisted laser desorption. Preferably, the method may further comprise steps of switching between ionization methods or of switching between ion polarities. Preferably, the method may further comprise a step of ion fragmentation being switched on and off at time scales of said chromatographic separation.

In another implementation, there is provided a tandem of fast IMS and MR-TOF for matching time scale of GC×GC or CE analyses. Such apparatus comprises: a gaseous ion source; a dual mesh gate connected to RF signal or a ring shaped ion trap for accumulating and pulsed or mass dependent transfer of ions at gas pressure from 1 to 100 mBar; an ion mobility drift space past said RF mesh gate; a multi-reflecting time-of-flight mass spectrometer with an orthogonal accelerator; a signal generator providing frequent start signals with encoded uneven intervals for triggering both— IMS gate at mean frequency generally above 1 kHz and said orthogonal accelerator at mean frequency generally exceeding 100 kHz, wherein the pulse string duration is comparable to IMS separation time; and a data system with acquisition period matching the duration of said pulse strings and also providing IMS-MS spectral decoding with the account of the coded pulse intervals and of the intensity distributions within signal series. The pulse coded MR-TOF is expected to match the speed of the fast IMS without ion losses. Preferably, said tapered IMS section may comprise either an ion funnel; or an ion funnel with a central expanding and contracting sections; or a multipole set formed of multipole PCB sections; or a converging ion funnel further comprising at least one electrode on axis for radial repulsion with DC field.

The tandem of IMS with frequent and encoded pulsed MR-TOF generally allows significant shortening of IMS cycles and frequent IMS pulses at about 1 kHz or above, this way improving charge throughput of the tandem. Using wide bore open or coaxial ion gates and wide bore or coaxial IMS cell further improves charge throughput and according to own estimations brings the throughput of the tandem to approximately 1E+10 ion/sec matching ion currents emitted by modern ion sources.

In another implementation, there is provided a method of IMS-MR-TOF analysis at GC×GC time scale. The method comprises the following steps: Ion accumulation by RF field in-front of dual mesh or inside a ring shaped ion trap; a pulsed or mass dependent ion ejection encoded by a repetitive pulse string with uneven intervals and at mean frequency exceeding about 1 kHz; subsequent ion mobility separation at gas pressure from at or between about (1 to 100) mBar; spatial focusing of ion flow past said step of ion mobility separation; a pulsed orthogonal ion acceleration encoded by a repetitive pulse string with uneven intervals and at mean frequency generally exceeding about 100 kHz; Time-of-flight analysis of ion m/z within a multi-reflecting electrostatic fields; and a step of decoding information on ion mobility time, ion mass and ion intensity with the account of the encoded and uneven pulse intervals and on intensity distribution within signal series.

Preferably, said step of spectral decoding may employ a multi-dimensional algorithm for analyzing data clusters in a multi-dimensional space of chromatographic time, ion mobility time and flight time in MR-TOF for accounting for all ion signals of any particular m/z specie during its chromatographic and ion mobility peaks while analyzing time profiles of individual mass components. Preferably, the method may further comprise a step of either ion fragmentation, or ion declustering (soft fragmentation) between steps of ion mobility separation and of time-of-flight analysis. Preferably, the method may further comprise a step of deconvolution for accurate assignment of mobility time and for time correlation between product ions. Preferably, the method may further account mass-to-charge dependence of time delay between the exit of ion mobility spectrometer and mass spectrometric detector. Preferably, the method may further comprise a step of measuring centroids of mass spectral peaks in elementary spectra and converting profile data into stick spectra. Preferably, the method may further comprise a step of recording detector signal in a data logging format with the stamp of laboratory time prior to steps of deconvolution, decoding, and averaging. Preferably, the method may further comprise a step of transmitting ions within a time window at a spatial position of one ion reflection within said multi-reflecting electrostatic fields, and wherein said transmitting time window is adjusted with currently transmitted mobility time for mobility—mass correlated ion selection. Preferably, the method may further comprise a step of ion sequence inversion at slow ramping of DC field propelling ions through said RF barrier at said gating step.

In yet another implementation, a method of differential ion mobility measurement comprising the following steps: (a) separating ions in a mobility spectrometer at a first value of field strength along said mobility spectrometer; (b) separating ions in a mobility spectrometer at a second value of field strength along said mobility spectrometer; (c) Repeating said steps for several field strength, wherein said field strength is sufficient for varying ion mobility, and wherein the mobility spectrometer is filled with light gas like Helium or Hydrogen, such that to avoid ion fragmentation at relatively large field strength sufficient for detectable mobility variations; (d) during the whole mobility separation cycle, acquiring mass spectra with multi-reflecting mass spectrometer with orthogonal accelerator; wherein said orthogonal accelerator is triggered with an irregular pulse string such that pulse period is much shorter compared to ion flight time in said mass spectrometer and wherein interval between any pair of pulses is unique in the pulse string; and (e) analyzing results within at least two dimensions of ion mobility and differential ion mobility.

In another implementation, there is provided a method of comprehensive analysis (i.e., not losing analyte or signal at separation or analysis) within multiple analytical dimensions comprising mass spectrometric analysis in multi-reflecting mass spectrometer with frequent encoded pulsing and simultaneous analysis within at least three analytical dimensions of the group: (i) gas chromatography—GC1 or liquid chromatography—LC; (ii) second and nested in time gas chromatography—GC2 or capillary electrophoresis—CE; (iii) multi-mode or switching polarity soft ionization like ESI, APCI, APPI, PI, CI or GD; (iv) fast switching in-source fragmentation is-CID; (v) ion mobility separation—IMS; (vi) ion fragmentation past IMS; (vii) time-of-flight mass measurements of integer mass—m/z; (viii) accurate mass measurements with extraction of mass defect and of elemental composition—dM; and (ix) differential ion mobility obtained by alternating field strength in conventional mobility spectrometer filled with light gas—helium or hydrogen.

Preferably, stages of said multi-dimensional analysis are pulsed with encoded pulse strings having uneven intervals, wherein average intervals between pulses are shorter compared to peak profiles of the upstream separation stage, wherein signal is recorded in a data logging format preserving laboratory time information, and wherein principal mass components are calculated for summed spectra with summing time comparable to peak width of a prior separation; and wherein time profiles of the upfront separation is then reconstructed with time resolution comparable to said average interval between said frequent pulses.

According to yet another aspect of the invention, there is provided a method of tandem analysis comprising the following steps: (a) trapping ions in coaxial trap; (b) pulsed or mass dependent ion release out of said trap; (c) separating ions in coaxial ion mobility space with DC axial field; (d) providing radiofrequency field radial repulsion on one side of said cylindrical mobility separation space; and (e) Providing radial DC repulsion of ions towards said radiofrequency barrier. Preferably, for the purpose of reducing electrical capacity effects, the method further comprises a step of filling said mobility spectrometer with gas at gas pressure generally at or between about (1 and 10) Torr to provide at least partial dampening of radiofrequency motion; and a step of using RF frequency generally under about 1 MHz and with amplitude generally under or about 200V zero to peak.

According to yet another implementation, there is provided a method of tandem analysis comprising the following steps: (a) ionizing a mixture of analyte molecules in an ion source; (b) filtering an ion flow by either mobility or differential mobility spectrometer such that to pass through one separated ionic fraction in a time; (c) declustering or fragmenting said separated ionic fraction; and (d) analyzing said declustered or fragmented ion flow in multi-reflecting time-of-flight mass spectrometer with encoded frequent pulsing. Preferably, said step of mobility or differential mobility filtering comprises one step of the group: (i) ion differential mobility separation in a narrow electrode gap with transverse asymmetric radiofrequency field combined with transverse adjustable DC bias (FAIMS); (ii) ion mobility separation by axial DC field in the transverse gaseous flow (DMA); (iii) ion mobility separation in a transverse modulated electrostatic field within an axial DC field and axial gaseous flow (TM-IMS); (iv) ion mobility separation in atmospheric or nearly atmospheric linear mobility cell within axial DC field with formation of short ion packets by Tyndal gate (IMS); (v) a travelling wave ion mobility separation (T-wave); (vi) ion mobility separation by moving segments of uniform axial field (overtone IMS); and (vii) mobility separation with axial gas jet being opposed to DC field. The set of methods is proposed as a low cost alternative for high throughput tandem of ion mobility and mass spectrometer and is applicable to wide range of ionization methods, including conventional methods and methods of ambient ionization for rapid sample handling with minimal sample preparation. The method capitalizes on the following realizations: (a) ion losses at ion mobility filtering are compensated by high efficiency of frequent encoded pulsing within MR-TOF; (b) at the same time, the combination of mobility filtering and of ion declustering or fragmentation do dramatically improve ratio of signal to chemical background which otherwise would be limiting efficiency of the frequent pulsing in MR-TOF; (c) ion mobility filtering allows reducing ion losses within the interface usually having means for protection against contamination which now could be eliminated along with the associated ion losses; and (d) in cases of moderate sample complexity, the upfront chromatographic separation could be replaced by the mobility separation, thus accelerating the overall analysis, making separation more reproducible and reducing sample injection flow rate to save on sample. As an example, LC can be replaced by a DMA analyzer and sample may be injected at 10-100 times smaller flow rate, thus extending time duration of the same intensity signal.

BRIEF DESCRIPTION OF DRAWINGS

Various embodiments of the present invention together with arrangement given illustrative purposes only will now be described, by way of example only, and with reference to the accompanying drawings in which.

DETAILED DESCRIPTION

Figure 1:
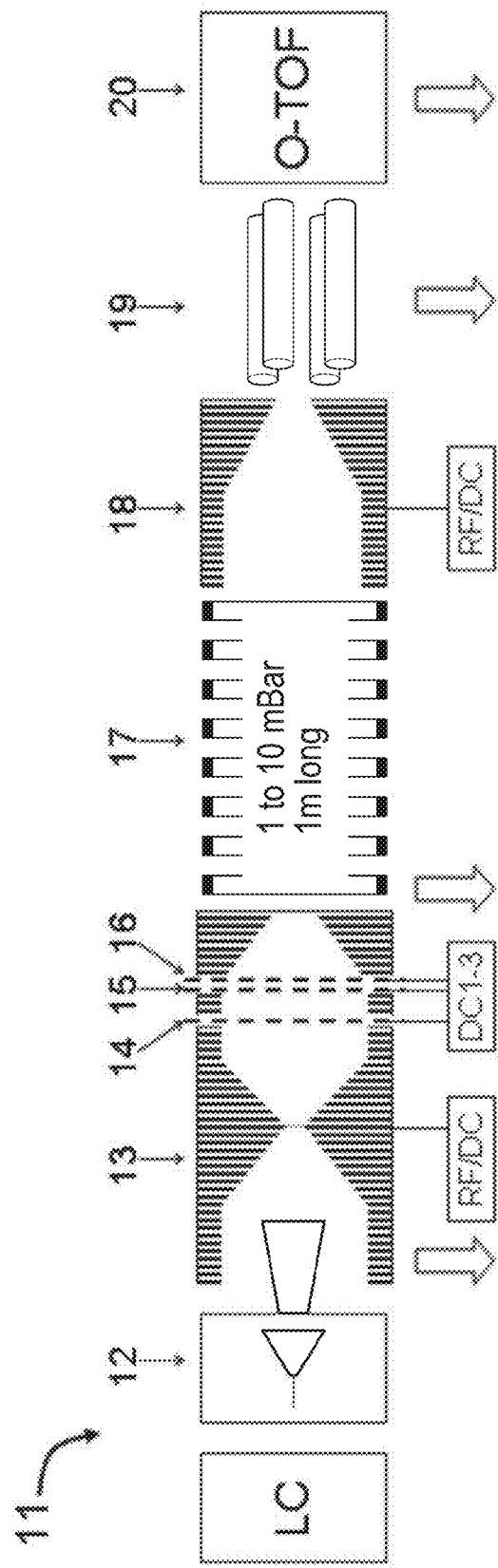
FIG. 1 depicts a prior art IMS with an hourglass ion trap and ion funnel at the IMS exit.

Referring to FIG. 1, a prior art (Anal. Chem., 2008, v. 80, pp. 612-623, incorporated herein by reference in its entirety) tandem 11 ion mobility spectrometer (IMS)—time-of-flight mass spectrometer (TOF MS) comprises the following sequentially combined components: an ion source 12, an hour-glass shaped ion funnel 13 connected to an RF signal with superimposed axial DC gradient, incorporated between funnel plates three meshes 14, 15 and 16 connected to switched DC signals for ion gating; an ion drift tube 17 filled with gas at pressure from at or between about (1 to 10) mBar, a second ion funnel 18 for converging the ion flow, a differentially pumped quadrupole ion guide 19 at gas pressure of at or between about (10-100) mTorr, and a differentially pumped singly reflecting time-of-flight mass spectrometer with an orthogonal acceleration 20. Pumping is shown by white arrows. Some of RF and DC supplies are shown by boxes. Electrospray (ESI) ion source is shown by schematic view of ESI droplet plume, and the gas jet past the source—by a light colored cone.

In operation, liquid chromatograph (LC) separates analyte molecules in about 1 hr time, while typical width of LC peaks may be at or between about (5 to 20) s wide. ESI ion source 12 ionizes analyte molecules while generating either M+ or MH+ ions. Ions are delivered by gas jet via a nozzle into the first ion funnel 13 region and get confined by the ion funnel 13. The gate accumulates ions in-front of the mesh 15 due to the weak (few Volts) DC bias between meshes 15 and 16. An extracting pulse is periodically applied to meshes 14 and 16 to drive ions through the mesh gate. The ion flow is then converged spatially prior to injection into electrostatic drift tube 17. Ions are then separated by mobility in the drift tube 17, get spatially confined by the second ion funnel 17, get transferred via the guide 19 and then analyzed by the TOF 20.

Typical 1 m length of the drift tube and typical (at or about (20-50) ms) IMS drift times are required to reach resolution of at or between about (30 to 50), since a typical width of ion packets is generally at or between about (200-400) us. The ion packet width may be limited by several factors, including: (a) ion packet spreading by space charge in the IMS drift tube; (b) ion packet spreading within the second ion funnel 18 and within the quadrupole ion guide 19, and (c) by a slow (100 μs) pulsing period of the TOF. Such separation speed is adequate if using an upfront liquid chromatography (LC), however, it is not sufficient for use with faster separation methods like GC×GC or LC×CE. The DC gate of IMS 11 is capable of storing and ejecting up to 1E+7 ions per pulse and the mesh gate gets saturated in 1 ms fill time. Thus, the duty cycle of IMS is 2-5% only. Higher ion loads are expected to affect resolution of IMS separation due to space charge effects in the hourglass gate and in the drift tube.

Fast Gate and Fast IMS of the Present Invention

Figure 2:
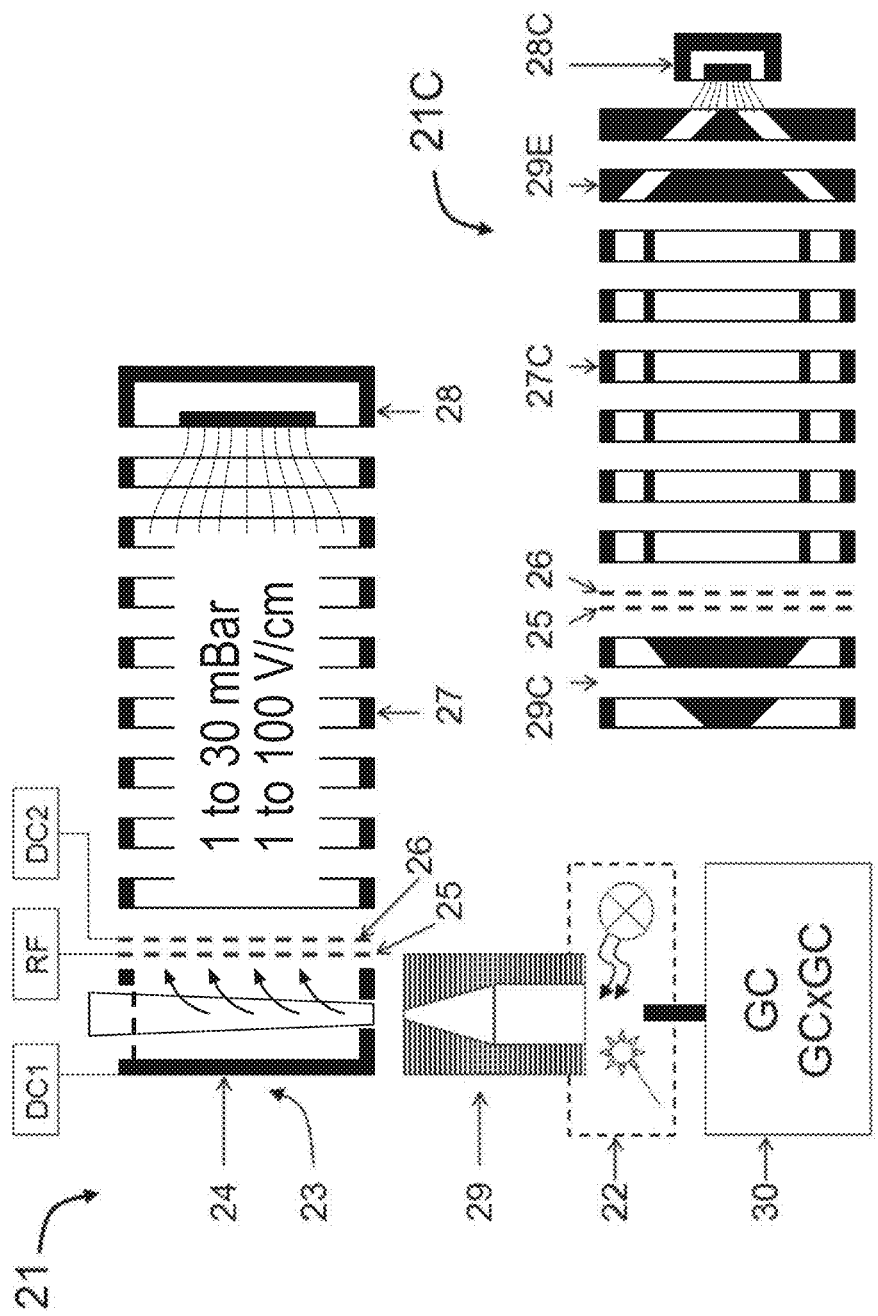
FIG. 2 depicts an embodiment of dual mesh gate with RF field between them and an embodiment with coaxial IMS.

With reference now to FIG. 2, an embodiment 21 of an IMS is shown comprising the following sequentially combined components: an ion source 22; an ion gate 23 formed of a front DC cap 24 electrode, a front mesh 25 with an RF potential and a back mesh 26 with a DC bias; a drift tube 27 formed of DC biased guarding rings to generate a generally uniform generally at or between about (10 to 100) V/cm electrostatic field and filled with gas at pressure from generally at or between about (1 to 100) mBar; and an ion detector 28—a collector electrode connected to an amplifier and signal recorder. To reduce time constant RC and capacity C of the collector, the electrode may be made of fine mesh. To ensure full ion collection the mesh is backed by an electrode with a retarding DC potential. The same collector mesh helps forming a ~1 m/s uniform counter-flow gas flow 27F along the drift region 27. Some critical power supplies are shown as schematic boxes.

Preferably, the IMS may be preceded by a dual stage gas chromatograph (GC×GC) for rapid separation of analyte mixtures. Typical width of chromatographic peaks is generally at or about 50 ms. After separation in GC×GC, the source 22 ionizes semi-volatile analyte molecules generally at or about between (100-1000) mBar gas pressure. In an implementation, ions may be focused by an optional ion funnel 29 to achieve generally optimal gas pressure in the gate 25, 26 and mobility 27 sections. A gas flow 22F may deliver ions into the gate 23 region operating generally at or about (10-100) mBar region. In an implementation, the gas flow 22F is generally oriented parallel to and above the mesh 25, to thereby retain meshes in a flow-quite zone. A DC bias applied to cap electrode 24 can generally push ions from the gas jet 22F towards the meshes as shown by arrows. Preferably, an RF channel with slight DC gradient (not shown) is inserted between the DC cap 24 and mesh 25 to avoid gas stirring by the jet flow 22F while sampling ions from the flow by a weak DC field.

In an implementation, the mesh 26 generally shields the mesh 25 from the strong (generally at or between about (10-100V/cm)) electrostatic field of the drift tube 27. In an implementation, the RF signal applied to mesh 25 can form a generally strong RF field between closely spaced meshes 25 and 26 thus retarding ions in the close vicinity of meshes. A balance of the long acting and attracting DC field with short acting and repelling RF barrier forms the ion trapping region in the close vicinity of the front mesh 25. For a pulsed ion ejection, a pulsed DC bias is applied to cap 24 (or front mesh of the RF channel 25), and/or mesh 26. Alternatively, for a mass-dependent ion release, the DC bias is ramped smooth.

Figure 3:
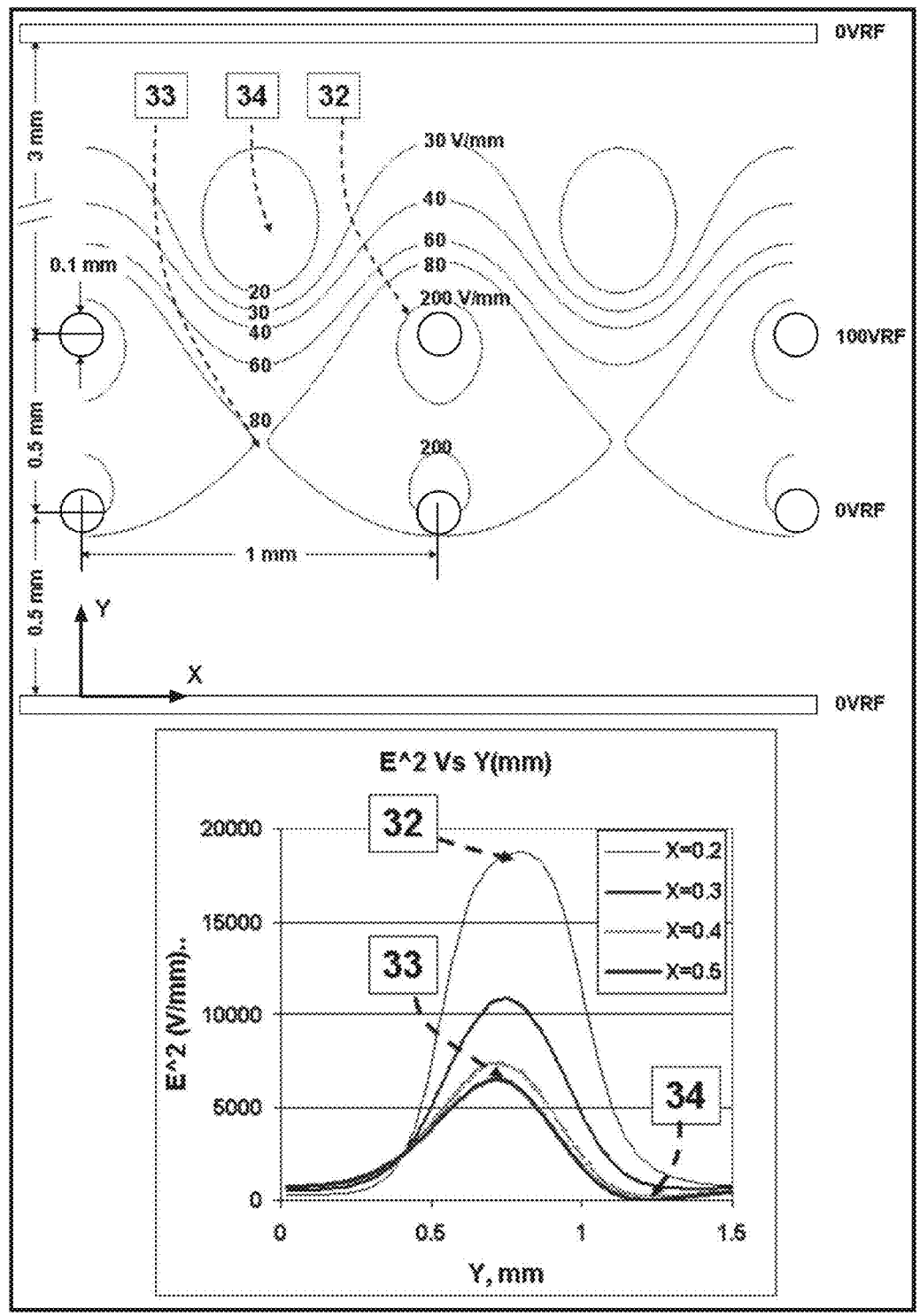
FIG. 3 shows lines of equal field strength within the ion trapping, according to an implementation.

Referring to FIG. 3, the lines of generally equal field strength within the ion trapping gate 23 are shown for one chosen exemplar gate with at or about 1 mm distance between meshes, at or about 0.1 mm wire thickness and at or about 0.5 mm distance between wires in each mesh, and at or about 100V amplitude of the RF signal. Lines of generally equal field strength E are annotated by numbers. The effective potential of the RF field is known to be proportional to $E^2 q/m\omega^2$, where q and m—ion charge and mass, $\omega$—is the RF frequency. Thus, higher field strength corresponds to a higher potential and ions get retarded from regions of higher field strength. Also note that the RF potential is mass dependent. As one can see, there is formed a retarding RF wall 32 around wires, there is also formed a saddle barrier 33 in the center between wires which prevents ion penetrating through the RF barrier at sufficiently small DC field. There is also formed an RF trapping region 34, in which the RF signal is eliminated (quadrupole origin of the RF field) and DC fields of the cap 24 and of the back mesh 26 can be balanced. The graphs show vertical $E^2(Y)$ profiles at various X distance from wire center. The above described regions 32-34 of the trapping gate are indicated on the graph.

Figure 4A:
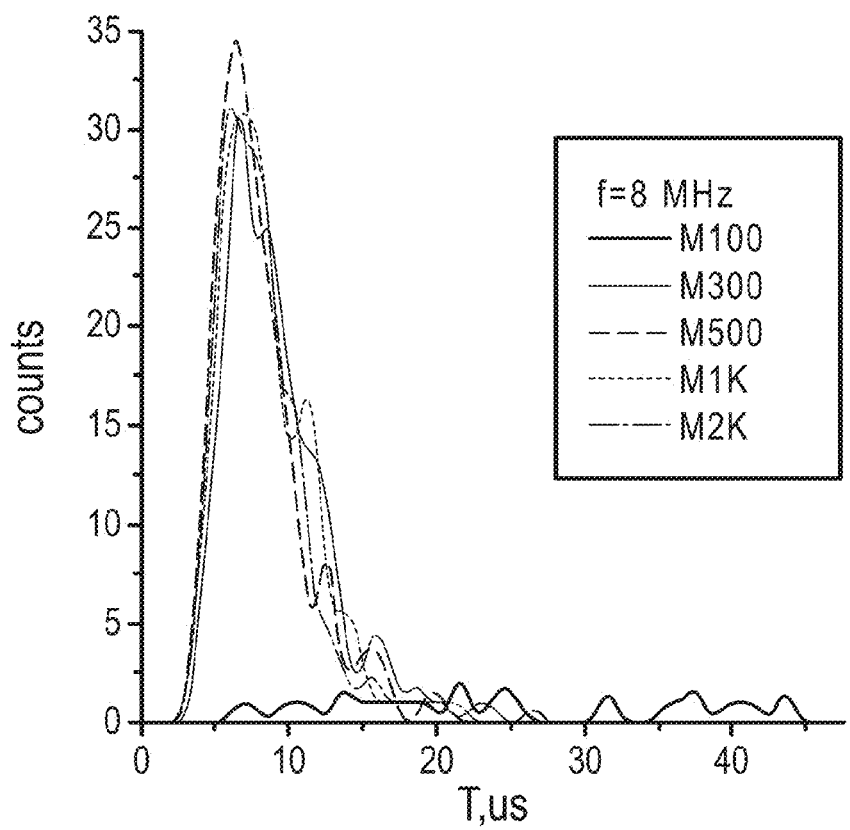
FIG. 4A depicts profiles for effective RF potential in the ion trapping gate, according to an implementation.
Figure 4B:
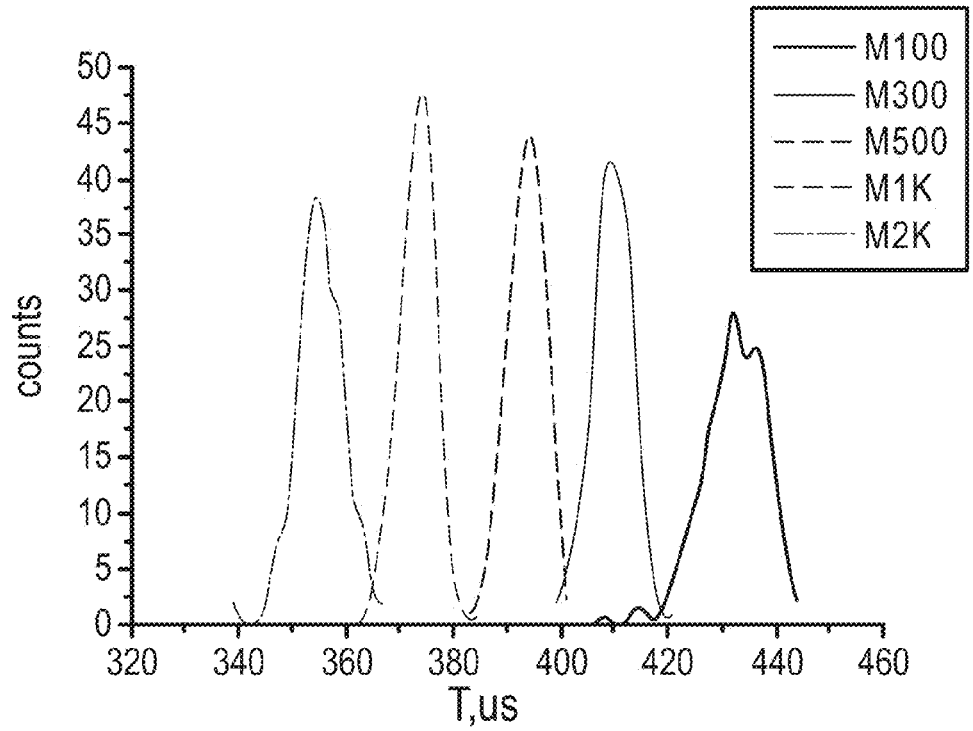
FIG. 4B depicts DC potential profiles at a stage of ion passage through the gate, according to an implementation.

FIG. 4A depicts simulated time profiles for ion current past the gate at a stepped ejection by an approximately 50V pulse applied to the mesh 26, at gas pressure of approximately 10 mBar, and at approximately 100 V/cm DC field of the drift tube 27. Note that ion packets can be as short as about 10 μs, which is explained by precise localization of ions in trapping region 34 prior to the ejection step. FIG. 4B depicts time profiles of various m/z ions with simulated cross section proportional to (m/z)^2/3, and at a ramped DC ejection with the DC potential on the mesh 26 varied as 0.2 V/us. Since the effective potential of the RF barrier is mass dependent, the small m/z ions would pass first, which generates a mass inversion (in all other regions small ions pass faster). In one particular method, the inversion is arranged such that ions with a particular ratio of mass and mobility arrive to the detector simultaneously, such that to analyze only ions of the particular chemical class (for example, aromatic compounds, while excluding linear molecules).

Multiple other arrangements of meshes are feasible. Sets of parallel wires forming meshes may be either aligned or shifted half step in the transverse direction. To avoid parallel alignment of two wire sets, the second mesh may be a square cell mesh with much finer cells. The first mesh may be a mesh with crude cells having square, rectangular, or hexagon shapes. The RF signal may be applied to the second mesh as well, which would have negligible effect onto the ion motion in the drift region. Ion trapping stage may be assisted by a small retarding DC bias between meshes. The ejecting DC field may be applied to either a cap, or any of meshes.

With reference now to FIG. 2, another implementation 21C for high charge throughput IMS comprises a mobility cell 27C arranged between coaxial cylinders while using conical RF funnels or conical ion guides 29C and 29E on both entrance and exit sides of the mobility cell 27C. In the coaxial mobility cell 27C, at least one cylindrical wall acts as an RF repelling surface and another provides electrostatic radial repulsion, such that ions are softly pushed onto the barrier. The radial field should be chosen just sufficient to oppose ion diffusion. A stronger field may induce stronger RF excitation and time spreading. In one embodiment illustrated in FIG. 2, the mobility cell is formed by rings. Such rings could be held together for example by tangential rails and being attached either by pins or by glue. The axial gradient field is arranged by applying voltage gradient between edges of the mobility cell 27C. Within each set of electrodes (one set corresponds to external cylinder and another to the internal one), said rings electrodes are interconnected via a resistive chain to form a uniform field gradient. An RF signal with alternated phase is applied to one set of electrodes, as an example to external rings, thus forming an RF barrier repelling ions from the outer wall. To keep ions close to the RF barrier, the DC potential on the internal set of electrodes is biased positive. Alternatively, the inner cylinder is also fed with an alternated RF, thus creating an RF ion channel. In the latter case, the gas pressure should be lowered under 0.1-1 mBar to provide effective ion mixing between the central and radial parts of ion flow. Alternatively, the RF barrier may be formed with short segments for arranging multipolar RF field and an axial DC field. Such electrode segments could be formed as printed conductive strips on flexible antistatic plastic, or can be formed as stamped brackets attached through holes in plastic, and the soldered or glued.

In operation, ions are driven by DC gradient towards the entrance RF ion funnel 29C and then are converged into a ring shape cloud at the funnel 29C exit. Periodically, the balance between axial DC gradient and the RF barrier of gate 25/26 is pulsed or the DC gradient is adjusted to admit either a short pulse or a mass dependent ion string. Ring shaped ion packets are pushed by DC radial field towards the radial RF barrier and travel along the radial RF barrier while being driven by the axial DC field within the cell 27C. Optionally, at the exit of IMS cell 27C ions are confined within an exit conical and coaxial ion funnel 29E towards a small size collector with small capacitance.

The embodiment 27C capitalizes on one novel realization. It has been believed that the RF field affects resolution in IMS due to ion heating. Instead, based on ion optical simulations it became clear that RF field generally does not affect resolution, but rather introduces a time delay between an axial portion of ions which are not excited by the RF field compared to radial portion of ions which are RF excited. Thus, the IMS resolution may be recovered either by effective numerous mixing of those two portions or by exposing all the ions to approximately the same RF excitation. The realization allows employing ion radial confinement by RF fields without affecting the IMS resolution in cylindrical and conical ion guides.

Since ions are confined by radial RF barrier and DC radial repulsion, the cylindrical mobility cell may be operated without ion losses and without additional time spreading usually occurring in RF ion guides. If applying RF confinement to both cylinders, the IMS with radial confinement still may operate at moderate ring thickness. Since the conical funnel does not introduce additional time spread compared to conventional ion funnels, the IMS cell may be operated faster while retaining the same level of IMS resolution. Thus, though the total charge capacity of the coaxial IMS cell becomes lower compared to wide open tubular cell, the space charge throughput gets recovered in the coaxial IMS cell due to faster cell operation.

Again referring to FIG. 2, the embodiment 21C preferably operates at relatively high gas pressure generally at or between about (1 and 10) mbar to provide partial dampening of the RF ion motion. This allows using much lower RF frequencies in the range of generally at or between about (0.5-1) MHz and much smaller RF amplitudes from generally at or between (50 to 200) Vo-p. The combination generally addresses the problem of large electrical capacitance of RF driven electrodes. In an implementation, if using regular RF parameters of generally or between about (3-5) MHz and generally at or between about (1000-2000) Vo-p, typical for ion guides ranges at lower gas pressures, the electrical capacitance in the order of about 1 nF will become a strong obstacle on the way to practical IMS implementation.

Also note that while wide bore IMS 21 requires the novel RF mesh gate with wide emitting surface, the coaxial IMS cell 21C may be effectively operating with other types of radiofrequency traps, such as ring shaped ion trap with radial ejection, an ion runnel or an ion funnel.

Numerical Example and IMS Parameters

It is to be understood that the numbers referenced in this example are approximate and the scope of the protected subject matter should not be limited to the specific examples described herein. Again referring to FIG. 2, in one numerical example, the distance between meshes 25 and 26 is 0.5 mm and mesh 25 is formed by parallel 50 um wires spaced at 1 mm. The open area of the gate is 50 mm in diameter. The RF signal on mesh 25 has 8 MHz frequency and 100V amplitude. The cap 23 is at 10 mm distance from the mesh 25 and has potential of 2-10V. The field strength in the drift region is 100 V/cm at L=30 cm drift length and 3 kV across the drift cell. Gas pressure of about 10 mBar is sustained by mechanical pump in both—drift and gate regions, wherein 3000V across 30 cm is not expected to cause electrical breakdown. At such gas pressures the average ion mobility of relatively small ions (analyte is separated in GC) is in the 100 $cm^2/V*s$ range. The average ion drift velocity is 100 m/s, i.e., notably under thermal gas velocity. The average drift time is 3 ms. The detector is 30-50 mm disk (assuming ion focusing by increasing electrostatic field at the IMS exit) connected to an electrometer with the 1 MOhm impedance. An expected detector capacity is 10 pF and the time constant of the electrometer is 10 us.

Let us estimate whether such IMS can reach target resolution R=T/dT from 50 to 100 while fully utilizing incoming ion currents of 1 nA. First, the initial packet width $dT_0$<10 us does not limit R up to 300 at T=3 ms. Second, according to Einstein equation, the diffusion limit R~C*sqrt(U/kT)= 60*sqrt[U(kV)] allows R~100 at U=3 kV. To sustain the same resolution limit by the ion packet space charge, the space charge field has to be less than 0.5 V/cm, i.e., at least 200 times smaller than the external field (accounting expansion of both—front and back ends). Such field is reached at maximal charge density of 2E+5 charges/$cm^2$, and the entire 5 cm size packet is limited to 6E+6 charges per ion packet of individual mobility. At 3 ms period this corresponds to 2E+9 ions/sec per individual mobility component and is likely to match 1 nA current throughput matching ion currents generated in majority of soft ionizing sources, like photochemical ionization, corona, and glow discharge ion sources. Still, it is preferable removing light solvent or matrix ions by an additional mass filter. Such filter may be arranged with the same dual RF mesh located upstream of the IMS gate. Retarded ions may be blown off by a gas jet coming from the source. The same filter may be employed for controlling the amount of injected current either by balancing DC and RF fields with gas flow or by a pulsed and ion admission at 10-100 kHz rate.

The cylindrical IMS cell 21C may be operated faster (say, once per 1 ms) due to smaller time spread at ion collection which allows using more frequent gate pulsing and using higher field strength in the IMS cell to improve resistance to space charge effects.

The dynamic range of IMS is limited by maximal signal on high end (defined by space charge limit of 6E+6 ions per pulse per component) and by the detector amplifier noise on low end. The Jonson noise of an amplifier is about 30 uV at 100 kHz bandwidth (matching IMS peak width and filtering out RF signal of the gate). The maximal signal of 6E+6 charges (1 pC) at 10 us peak time corresponds to 1 uA current and 1V signal at 1 MOhm impedance. Thus, the dynamic range per single IMS shot is limited to approximately 10,000 assuming S/N=3 as detection threshold.

According to the above estimations, the IMS 21 is expected to operate at 3 ms period and to provide sufficient time resolution in GC×GC-IMS experiments, wherein the peak width past GC×GC 29 is expected about 50 ms.

Figure 5:
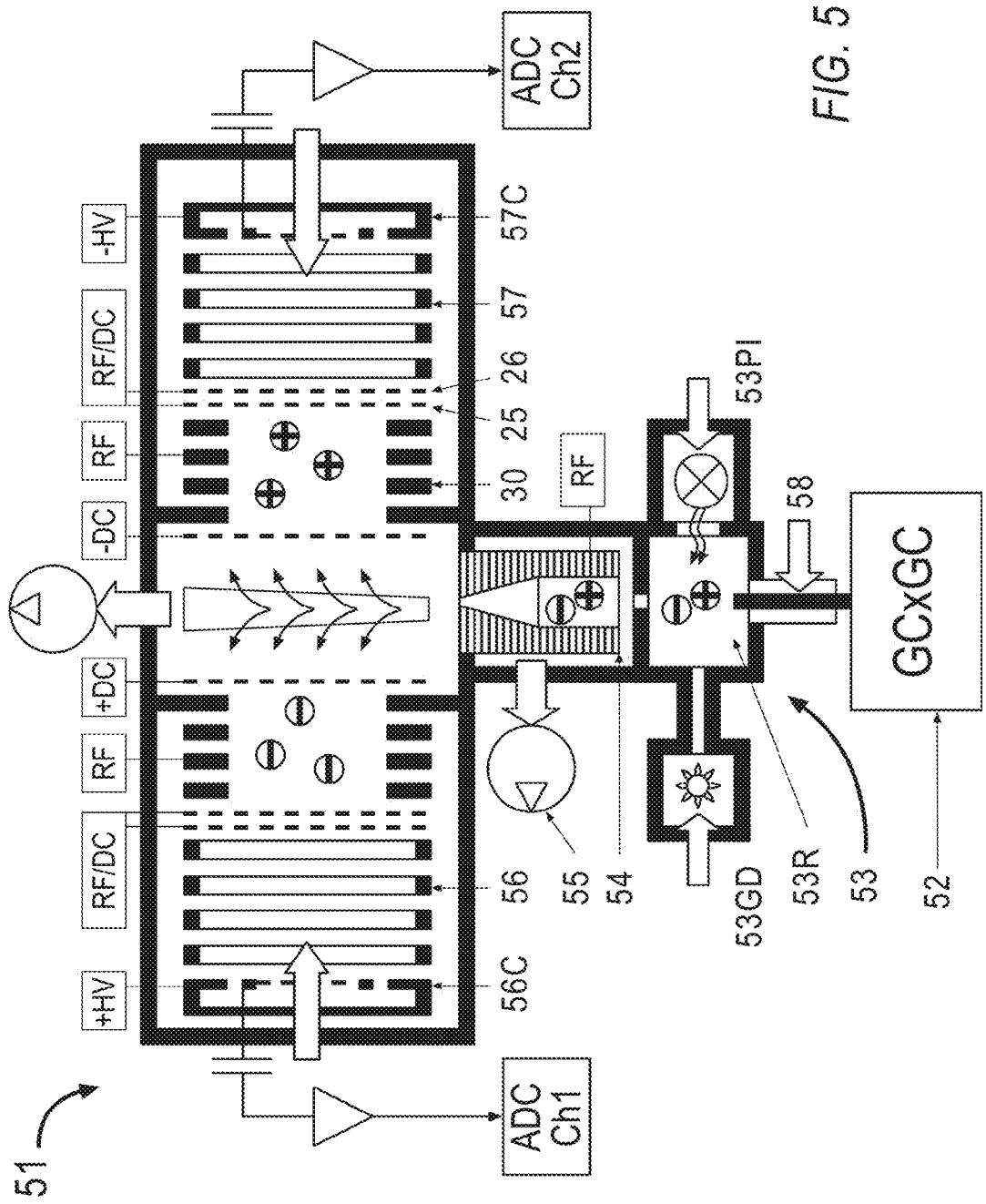
FIG. 5 shows and embodiment of IMS with dual mode ion source and dual drift cell, according to an implementation.

Referring to FIG. 5, an embodiment 51 of ion mobility spectrometer comprises a GC or GC×GC separator 52, a combined ion source 53 with multiple ionization modes and switching polarity of ionization. Such switching is preferably made between IMS scans. The source 53 operates at gas pressures from 100 mBar to 1 Bar. The ionization is likely to employ a carrier gas supply 58, assisting sample and dopant vapors delivery and adjusting pressure in the ionization region. Preferably, the source 53 is followed by an ion funnel interface 54, pumped to about 10 mBar gas pressure by a mechanical pump 55. The IMS instrument further comprises two drift cells 56 and 57 operating on both sides of the ion gate, each drift cell has own collector 56C and 57C, preferably connected to a single acquisition system 58 (0.5-1 MHz ADC with at least 16 bit vertical resolution).

Since GC employs clean gases and delivers low volatile analyte, the mechanical design of the GC×GC-IMS should satisfy several important considerations. The ion source and IMS components have to be heated preferably up to 250-300 C, to avoid absorption of analyte molecules onto walls. The IMS should use clean materials, like non porous metals, ceramics, and glass to avoid fumes. In some colder regions one may use Vespel and Kapton for insulation and Vespel or graphite for seals. Vacuum seals should be of metal-to-metal type, like Conflat and Swagelock to avoid outgassing materials. Drift cells may be a ceramic tube coated inside with a high impedance antistatic material, like tin oxide or conductive glass as provided by Photonics. Alternatively, a set of metal plate (e.g., ring) electrodes may be separated by ceramic balls and clamped by metal rods. Preferably, the electrode window should exceed the size of gate opening by at least one thickness of the plate. In one numerical example, the gate opening has 25 mm diameter, 4 drift electrodes are rings with 75 mm window and the drift region is 100 mm long. Preferably, a chain of resistors is located outside of vacuum region to avoid outgassing. Preferably, the ion source region is at near ground potential, while the back of the drift tube is floated, and collector signal comes via a capacitor. Preferably, the drift cell is surrounded by a shroud for (a) preventing gas stirring by the gas flow in the ion source region and (b) to provide a slow (1 m/s) laminar flow within the drift cell in order to prevent source fumes into the drift region. To avoid piezo-effects on collector, the mechanical pump should be vibration-decoupled, e.g., by a bellow, and should be isolated by an oil filter to avoid oil fumes. For economy reasons, a small size mechanical pump may be used to allow bench-top packaging of the IMS detector for GC×GC.

Multi-Mode Source for GC×GC-IMS

Referring now to FIG. 5, the ion source 53 may be selected from the group consisting of: (i) a photo ionization (PI) source; (ii) a photo-chemical (PCI) ionization source 53PI with dopant vapors; (iii) a chemical ionization (CI) source with proton transfer reactions; (iv) a negative chemical ionization (NCI) source with electron attachment ionization; (v) a glow discharge (GD) source 53GD with analyte ionization by conditioned products of glow discharge. A chemical ionization (CI) is provided by inducing a corona or few uA (limited by resistor) glow discharge. Dopants like ammonia, acetone, or amino-benzene would generate quasi-molecular MH+ ions, ionizing analyte molecules by proton transfer reactions. In NCI source, M-H− or M− ions can be formed at negative corona bias. Photochemical ionization (PI) 53PI is arranged by primary ionization of benzene or cyclo-hexane with xenon or argon UV lamp. Analyte vapors are then ionized in charge transfer (electron tunneling) reactions, primarily forming molecular M+ ions. As described in a co-pending application having Ser. No. 61/375,095, in a Glow discharge (GD) source 53GD the glow discharge products are conditioned to let electrons and most of the ions drift to walls of the delivering tube, while long-living meta-stable Helium or Argon atoms with about 20 eV excitation ionize analyte vapors in a separate 'reactor' volume, thus forming molecular M+ ions with moderate amount of fragments. The composition of those fragment ions is similar to those formed by electron impact, i.e., could be used for NIST confirmation, though GD ionization is softer and provides molecular ions for most of analyte molecules with negligible molecular ion intensity in EI spectra. Ion sources like CI may be switched in ionization polarity by reverting potential on ionizing corona discharge. Ion sources like PCI and GD are capable of simultaneous generation of both polarities ions and may be combined within one source via a common reactor chamber 53R. Ionization mode may be switched by regulating gas flows (shown by white arrows), or switching glow discharge or turning UV lamp on and off. Based on the described properties of CI, NCI, PI and GD sources, GC×GC-IMS 51 with rapidly switching multiple ionization modes is expected to provide several important analytically properties, such as: (i) characterization of analyte mass which is roughly correlate with ion mobility; (ii) an additional selectivity of ionization which carry such information as ionization potential, proton or electron affinity and presence of polar groups; (iii) ability of ionizing wide range of analyte classes; and (iv) adding specificity by selective ionization. Such ability may be considered as an additional analytical dimension.

The GC×GC-IMS instrument is expected to be a useful tool for characterizing complex mixtures and for detecting ultra-traces. The GC×GC is known to separate compounds by classes (see application notes on the web site www.leco.com). In some samples, like diesel or crude oil, multiple isomers do form characteristic patterns in two-dimensional (2D) space of retention times RT1 and RT2. Often, target compounds, like halogenated toxic compounds, are separated in 2D space from the majority of matrix compounds. It is expected that instant IMS spectra would be much less complicated compared to conventional direct IMS analysis. Then the information on the mobility of molecular ions may be obtained. Ion mobility is expected to become a third analytical dimension of the 3-D GC×GC-IMS analysis. On a fly alternation of ionization modes with additional ionization selectivity can be considered as a fourth analytical dimension. Note that capability of 3-D and 4-D GC×GC-IMS analysis appears only with introduction of sufficiently fast IMS of the invention and its combination with fast and soft ionizing ion sources.

Fast IMS with Frequent Pulsing MR-TOF

In one group of embodiments and methods, according to an implementation, an accelerated IMS is coupled to a high resolution multi-reflecting time-of-flight (MR-TOF) instrument which operates at frequent and encoded pulsed injection. Frequent encoded pulsing supports high speed of the IMS separation (resolves rapid IMS profiles), eliminate space charge saturation in IMS and IMS gate, and enhances the duty cycle of an MR-TOF or an open multi-reflecting Electrostatic trap (EMS), as described in a co-pending applications WO2011135477A and WO2011107836, incorporated herein by reference in their entirety. To enhance the decoding step and to improve sensitivity and dynamic range of analyses, a frequent encoded triggering may also be applied to the IMS gate. Note that encoding of IMS gate is not fully necessary. MR-TOF is capable of detecting accurate mass with sub-ppm mass accuracy and is capable of tracking individual mass components. Thus, IMS gate could be pulsed as frequent as long mass components do not overlap in time, or unless frequent encoded mass spectra become too populated. Several estimations suggest that generally at or between about (0.5 to 1) ms period of IMS gate pulsing is about optimal.

Figure 6:
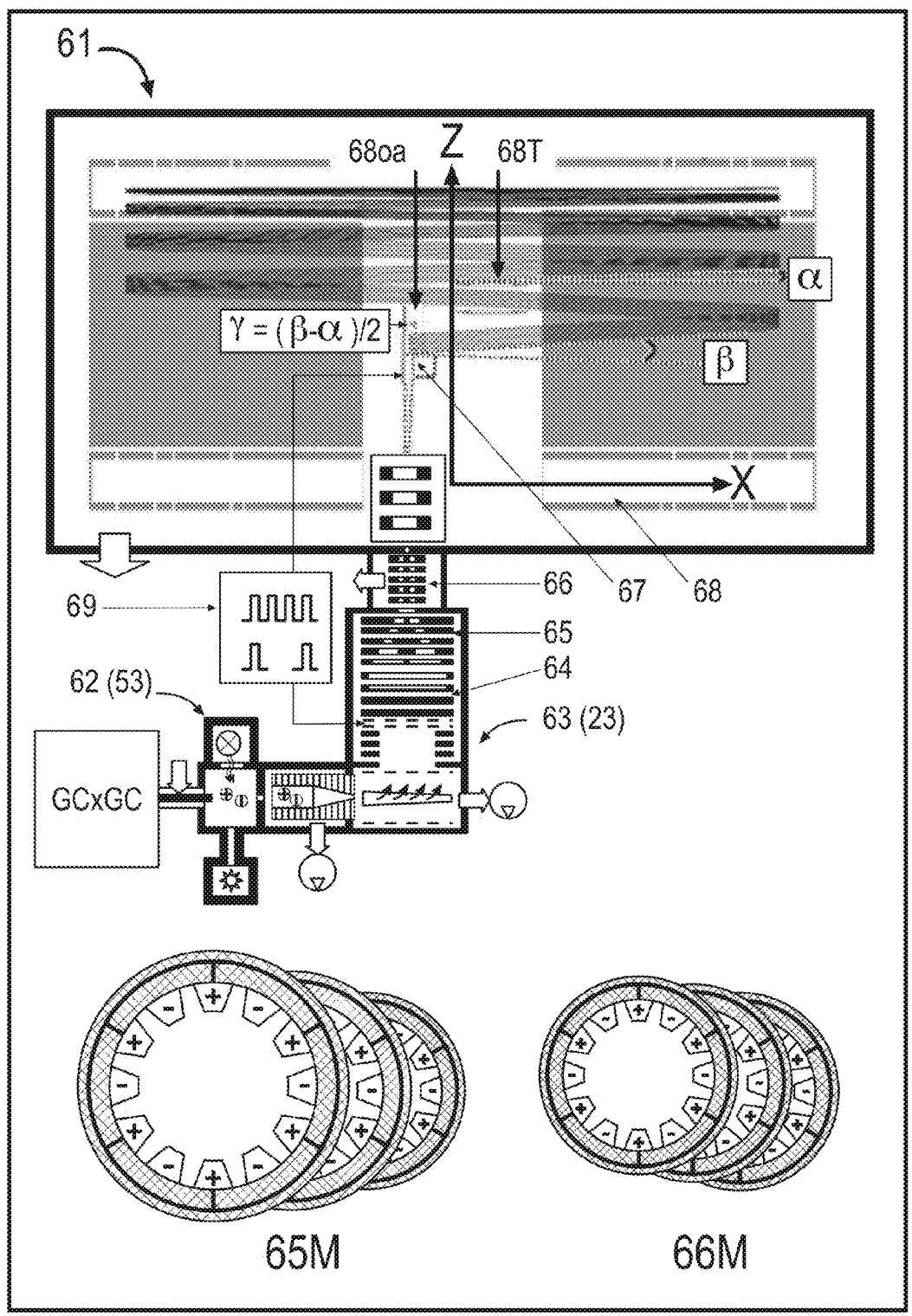
FIG. 6 shows an embodiment of GC×GC-IMS-MRTOF with the fast encoded pulsing of an orthogonal accelerator, according to an implementation.

Referring to FIG. 6, the exemplar embodiment 61 of the IMS-MR-TOF of the invention comprises the following sequentially combined components: an above described multi-mode ion source 62 (53), an above described ion gate 63 (23), an ion drift tube 64 filled with gas at pressure from generally at or between about (1 to 100) mBar, a tapered IMS section 65 for converging an ion flow, a differentially pumped ion guide 66, an orthogonal accelerator 67 with fast coded pulsing at mean frequency generally at or between about (100-200) kHz; an MR-TOF analyzer 68; and a data system 69 providing coded start signals for triggering ion gate 63 and OA 67 with the string duration comparable to IMS separation time and also providing IMS-MS spectral decoding with the account of the coded pulse intervals and based on time profiles for encoded signal families corresponding to individual mass components. For the sake of rapid ion transition, said tapered IMS section 65 may comprise either an ion funnel with a central expanding and contracting section 65T (since major delay and, hence, time spread occur due to ion travelling along the ion funnel surface), or a multipole set 65M with an axial DC gradient formed of multipole sections, preferably made of PCB stack. Preferably, the ion guide 66 is also made as multipole with an axial DC gradient, made of PCB stack, or rods of resistive material such as silicon carbide or carbon filled resistors 66M. Alternatively, a segmented multipole ion guide is formed using sheet metal brackets inserted into an isolative cylinder. In spite of axial DC field in the tapered section 65, still there appears a time difference between axial and radial distant portions of the ion flow with additional time spread, estimated in the order of generally at or between about (30-50) µs. To maintain IMS resolution above 50 the IMS drift time should be then increased to generally at or between about (2-5) ms. In an embodiment, doubling IMS length and voltage may be preferable compared to stand-alone IMS of FIG. 5. Preferably, the coaxial cylindrical IMS cell 21C is employed as shown in FIG. 2. The conical ion funnel or tapered ion guide 29E does not introduce an additional time spread, since all the ions are exposed to the RF barrier and there is no central portion of the ion flow which would travel faster. Preferably, the MR-TOF analyzer 68 is either a planar MR-TOF or a cylindrical MR-TOF described in a co-pending application having Ser. No. 61/552,934. The expected flight time in MR-TOF is in the order of generally at or between about (1-2) ms. Preferably, IMS-TOF 61 is preceded by a fast chromatograph 70—LC×CE, GC, or GC×GC. Alternatively, the IMS cell replaces the chromatography for higher throughput analyses.

In operation, GC×GC 70 separates analyte molecules and elutes them sequentially, wherein GC2 peak duration is about 50 ms. The example is chosen as most stressful on the apparatus timing. Note that in case of using GC or CE chromatographic peaks are about 0.5-1 second wide and in case of LC—about 3-10 seconds wide. The ion source 62, either CI, or PI, or soft GD (or ESI, APCI, APPI in cases of LC and CE) ionizes molecules and forms primarily M+ or MH+ ions. The ion source 62 operates at gas pressures from generally at or between about (100 to 1000) mBar and IMS at generally at or between about (10-100) mBar. In an implementation, differential pumping may be provided by mechanical pumps, equipped with fume filters. Differential pumping can form a gas flow between stages. Preferably, gas jet is oriented parallel to the gate 63 and with an offset from the gate to avoid gas stirring. A DC bias of the cap 23 drives ions towards mesh 24. An RF signal between meshes 24 and 25, retards ions in the close vicinity of the meshes. Ions get stored within local traps in front of mesh 24. Periodically, a DC pulse or a DC ramp is applied either to the cap 23 or to the back mesh 25 to extract short (about 5-10 µs) ion packets. Ion packets are separated by mobility in the drift region 64 (within generally at or between about (2-5) ms mobility drift time), get converged in the tapered section 65, rapidly pass through the ion guide 66 (being driven by axial field), get into the pulsed extraction region 67, got pulsed accelerated into the cylindrical MR-TOF 68 for mass separation. The IMS separation may be enhanced by vapors of organic solvents to separate by difference in ion clustering reactions.

Figure 7:
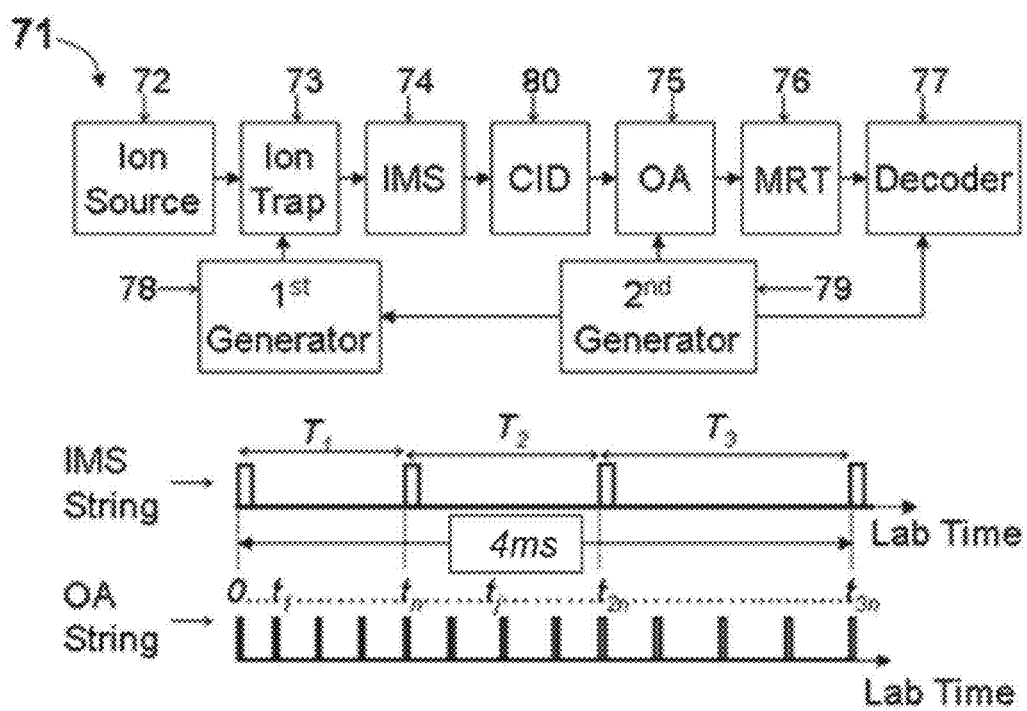
FIG. 7 shows a block scheme and time diagram for apparatus of FIG. 6, according to an implementation.

Referring to FIG. 7, the tandem 61 (71) is shown on the level of block schematic accompanied with the time diagram. The tandem spectrometer 71 comprises: an ion source 72; an ion trap 73 (here dual RF mesh or a ring-shaped RF trap) being triggered by a first encoding pulse generator 78 which forms an IMS pulse string (i.e., cause ion injection from ion trap 73 into IMS drift region 74); an ion mobility spectrometer drift tube (IMS) 74, followed by a tapered section and by an ion guide with axial gradient (not shown); an orthogonal accelerator (OA) 75 being triggered by a second encoded pulse generator 79 which forms OA pulse string; an MR-TOF analyzer 76; and a data system with spectral decoder 77. Optionally, as will be described in the next section, a CID fragmentation cell 80 is inserted between IMS 74 and OA 75.

Fast 2-D Encoding:

Referring to timing diagram of FIG. 7, rapid operation of IMS-TOF instrument 61 is the primary concern, since GC×GC forms very narrow (~50 ms) GC2 peaks. Also note, that the expected IMS separation time is generally at or between about (2-5) ms and the expected MR-TOF flight time is generally at or between about (1-2) ms (i.e., only at or between about 10 to 25 fold shorter compared to GC2 peaks.) Thus time scales between tandem stages are close enough to prevent conventional tandem operation with a sequential scanning of IMS and HRT.

To fit stressful overall timing requirements where time scales of sequential separation stages are close, the novel method is suggested where tandem stages are triggered with overlapped encoded pulse strings having uneven (!) intervals, wherein string duration matches data acquisition period, and wherein average time intervals between pulses are selected short enough to recover time profiles of upstream analytical stage. Here the IMS gate 73 is driven with a first pulse string 78 (optionally encoded) with an average interval of at or about 500 µs—sufficient to recover about 50 µs GC2 profiles, and the OA 75—with the time encoded second pulse string 79 with an average interval generally at or between about (5-10)µs, sufficient to recover IMS profiles with expected generally at or about (30-40)µs peak width. Both pulse string generators 78 and 79 provide pulses with uneven intervals and both generators are synchronized to fit into generally at or about (2-4) ms length of acquired spectra.

For clarity let us follow one particular numerical example (again understanding that the numbers used in this example are approximations): Pulse time of first generator 78 (driving IMS gate) is defined as $T(n)=n*T_1+T_2*n*(n-1)$; wherein with $T_1=360$ us and time increment $T_2$ is 40 us exceeding IMS peak width; index n is integer from 0 to 8; $T(8)=4$ ms exactly, i.e., coincides with $T(0)$ of the next string; and spacing between adjacent pulses varies with 40 us increment from 360 to 640 ms. Time string of the second generator 79 (driving OA) is $t(i)=i*t_1+t_2*i*(j-1)$; where $t_1=10$ us; time increment $t_2=10$ ns exceeds peak width in MR-TOF; indexes i and j are integer from 0 to 341; $t(341)=3,989.7$ us and $t(342)=4$ ms exactly, i.e., coincides with $t(0)$ of the next cycle; and spacing between adjacent pulses varies with 10 ns increment from 10 us to 13.42 us with the only exclusion for last pair of pulses.

Mutual alignment of pulse strings may be optimized in various ways. In one method, the first generator 78 may be triggered at every $m^{th}$ start of the second generator 79. In another method, the strings may be intentionally shifted such that to improve resolution of IMS profiles. Yet in another embodiment, within the second time string, the index j is varied (though fixed for the entire analysis) relative to index i, such that to alternate shorter and longer pulse intervals and this way to minimize slow and small variations in pulse generator load. The signal at the MR-TOF detector may be summed for several string cycles, say for 8 or 12 ms, such that to follow 50 ms peak profiles past GC2. Alternatively, signal is recorded in a so-called data-logging format, preserving time information while allowing integrating signals at the decoding and data analysis stages. The string formulation assumes signal overtaking between adjacent strings (i.e., some signal continue coming from previous pulse string). Assuming overtaking, and accounting strong correlation between IMS drift time and MR-TOF flight time, one may use shorter pulse strings (say 2 ms). Intervals between pulses and string duration should be selected depending on the required chromatographic speed and on spectra complexity. Also note that encoding of the IMS gate is not fully necessary. MR-TOF is capable of detecting accurate mass with sub-ppm mass accuracy and is capable of tracking individual mass components. Thus, IMS gate could be pulsed as frequent as long mass components do not overlap in time, or unless frequent encoded mass spectra become too populated. Several estimations suggest that 0.5 to 1 ms period of IMS gate pulsing is about optimal.

Decoding Principle:

As described in the co-pending application WO2011135477, every m/z component is expected to form a group of at least several MR-TOF peaks corresponding to sequential OA triggers. Due to multiplicity of IMS starts, the groups would be spread between multiple IMS starts, which helps in forming representative peak groups (30-40 peaks are expected in the above numerical example). Then, because of unique intervals in the OA string, time intervals between peaks would allow deciphering of both—actual OA firing time and flight time in MR-TOF. The OA firing time is related to IMS separation time. The distance between sub-groups in peak groups (corresponding to various IMS starts) is then matched to IMS time intervals to allocate the pulse number of the first generator and this way to calculate IMS time. The mobility drift time is then confirmed by flight time (accounting their weak correlation). The overall spectrum is decoded for recovering multiple groups and their overlaps. In the simplest decoding algorithm the overlaps are discarded. In a more advanced and faster deciphering procedure, the groups are analyzed for consistency in peak centroid and peak intensity, which avoids time-consuming procedure of determining overlaps between groups. The speed of processing is preferably enhanced by multi-core PC boards or multi-core imbedded processors. Intensity distribution within signal groups and between signal groups would serve to recover GC2 and IMS profiles.

Expected Result:

It is expected that the proposed method of overlapped fast encoded pulse strings having uneven time intervals would dramatically improve both—time resolution and sensitivity of tandem analysis with comparable time scales of tandem stages. Fast encoded pulsing improves duty cycle of IMS stage by eliminating space charge saturation of IMS and of the IMS gate, and improves the MR-TOF duty cycle by frequent pulsing of the OA. The spectral decoding would simultaneously recover (a) time profiles of GC2, (b) mobility profiles, and (c) the flight time in MR-TOF, and hence, m/z after MR-TOF calibration. If using data logging data system the GC2 profiles of 50 ms width will be tracked at about 500 us resolution of IMS gate pulsing, and IMS profiles of 30-40 us width will be tracked at about 5-10 us tracking resolution of OA pulses.

Multi-Dimensional Clusters:

Since both IMS and m/z information is expected to be obtained several times during any single GC or GC×GC peak, the spectral decoding should use the benefit of repetitive spectra—improve statistics and accuracy of m/z and mobility measurements, and use verification of weak signals. In more details, the decoding algorithm may pick up false positive m/z peaks by accounting randomly overlapping noise signals. However, such false positive peaks would not occur at the same m/z in several spectra in a row. Thus repeating of weak signals serves for their verification. Mathematically, the decoding should employ an algorithm for detecting clusters in multi-dimensional space formed by retention time of gas chromatography, mobility time, and coded time intervals between peak series.

Improved Mass Accuracy:

IMS separation makes momentarily mass spectra much sparser due to: (a) admittance of relatively narrow m/z range at particular IMS time (mobility is partially correlated with m/z); and (b) partial separation of fine isobars at any particular IMS time. Thus, partial time separation of mass spectral peaks by ion mobility improves both—detection threshold and mass accuracy of mass spectrometry.

Stick Spectra:

Since spread in centroid determination is much lower than peak width, it is preferable to convert decoded mass spectra into so-called stick format, wherein mass spectral peaks are presented by their laboratory time (for recovering GC and IMS time information), TOF centroid and peak area. Then any summed spectra would still allow separation of fine isobars at mass resolution being 10 times higher than resolution in profile spectra.

Logging Data System:

Preferably, the recording data system employs data logging format rather than summing of long spectra. As an example, non-zero segments of signal waveform may be recorded as [laboratory time stamp, flight time of first non-zero bin, sequence of non-zero intensities] for substantial data compression, so that the non-summed data flow may be passed via modern fast buses like PXI or multi-lane PCIe. The data flow is then preferably analyzed by a multi-core video board. Data logging format reduces data size, accelerates signal analysis, helps preserving time information of GC2 and IMS profiles, while improving ion statistics in mass spectra when signal is averaged (e.g., with sliding averaging) at the data analysis stage.

The tandem of IMS and rapidly pulsed MR-TOF is truly symbiotic. The upfront IMS separation simplifies the momentarily mass-spectral content and makes mass spectra really sparse and low populated in spite of strong spectral multiplexing. As a result, the spectral decoding becomes highly reliable and pulse frequency of MR-TOF could be pushed to the limits of time propagation through the OA, e.g., 3 μs. Such frequent pulsing may be supported with modern pulse generators, like Behlke switches operating up to about 3 MHz frequency. This in turn improves MR-TOF sensitivity and improves the time resolution of profiling, i.e., tracking time changes of the incoming ion flux. Another advantage appears due to isobar separation in the IMS. By nature, close isobars have different elemental compositions and are likely to be separated in IMS, as been demonstrated in multiple IMS publications, wherein different compound classes form isolated trend-lines in IMS-MS space. As a result, mass peaks become cleared from very close isobars and their mass could be defined with much better accuracy. A typical sub-ppm mass accuracy in determining mass peak centroids in MR-TOF corresponds to effective resolution of several millions in mass spectra composed of centroid sticks. Thus, the overall effective resolution of dual separation may be in the order of millions while using MR-TOF with typical resolution of about 100,000.

Rapid operation of the MR-TOF solves multiple problems of prior art IMS analyses. First, fast (10 us average) pulsing of the OA allows recording sharp time profiles of the up-front IMS, which in turn, strongly improves IMS charge throughput. The precise and time-resolved profiles allow much more accurate measurements of ion mobility compared to IMS resolution, which in turn is expected to improve characterization of complex samples based on multi-dimensional tags, as will be detailed below. Second, fast OA pulsing allows distributing large momentarily ion fluxes into multiple ion packets. Contrary, in prior art temporal concentration of ion flux within the IMS caused problems with saturation of the analyzer space charge and was stressing the dynamic range of the detector. Third, rapid cycling of the IMS-MR-TOF tandem makes the IMS-MS compatible with truly fast separation methods such as GC×GC and CE or allows rapid profiling at surface imaging experiments. Fourth, fast IMS-MR-TOF cycles allow varying experimental settings, the advantage is elaborated on the example of arranging differential mobility measurements without ion losses, as will be described in FIG. 11. Fifth, rapid MR-TOF operation allows truly parallel tandems, discussed just below.

All Mass Pseudo MS-MS

Again referring to FIG. 7, the embodiment 71 further comprises a fragmentation cell 80 between IMS 74 and OA 75. The fragmentation may employ prior art fragmentation methods like collision induced dissociation (CID), surface induced dissociation (SID), photo induced dissociation (PID), electron transfer dissociation (ETD), electron capture dissociation (ECD), and fragmentation by excited Ridberg atoms or ozone. The time diagram remains the same and the OA is operated with coded frequent pulsing (about 200 kHz) in order to track rapid changes of the ion flow after cell 80. Then the tandem 71 is expected to provide all-mass pseudo MS-MS at a time scale of fast chromatographic separation. In other words, the tandem provides massive parallel MS-MS analysis for all parents without losses of intensity and time while doing it at a speed of GC×GC separation. Such MS-MS is expected to be also achieved with sub-ppm mass accuracy and 100K resolution of MR-TOF for fragment ions.

In such combination the IMS is used for crude (resolution ~50-100) but rapid separation of parent ions and the MR-TOF is employed for even faster acquisition of fragment spectra. Optionally, in case of moderate ion flows, the encoding of the $1^{st}$ generator may be switched off. Preferably, the fragmentation cell (usually RF device) is equipped with means for ion accumulation and pulsed extraction and the OA pulse string is synchronized for the duration of the extracted ion bunch. The co-pending patent application WO2011135477 describes algorithms for decoding such spectra. In brief, the algorithm searches for MR-TOF peak series which are spaced according to the encoding time intervals, then allocates overlaps between series and may either discard or account such overlaps. Alternatively, series may be analyzed for consistency of peaks intensity and centroids, which allows an even faster decoding which may be highly parallel on multi-core PC or multi-core boards. Then each peak series allows allocating the corresponding OA start time and m/z of the component. The summed spectra are recorded with about a 100 Hz rate which allows recovering generally at or between about (30-50) ms profiles of GC×GC separation. Overall, the encoding allows compressing the time scale and obtaining about 10 ms time resolution of GC×GC analysis and about 10 μs resolution of IMS analysis in-spite of nested analysis in fairly slow IMS and MR-TOF devices with generally at or between about (0.5-2) ms flight times.

Parent Separation— few considerations have to be accounted to estimate true resolution of parent ion separation: (a) Though resolution of IMS is expected to be generally at or about a 50-100 range, the recovery of detailed IMS profiles with time resolution of the fast encoded pulsing (generally at or about 5-10 μs) would allow a more accurate recovery of IMS peak centroid. Then the separation capacity of parent ions is expected to be above 200—(1-2 ms per 5-10 us steps) and matching resolution of parent selection in conventional MS-MS with sequential selection of parent ions; (b) The families of fragment ions could be gathered by so-called deconvolution procedure by coincidence of IMS times. The procedure has to account mass correlated delay within the fragmentation cell which can be calibrated in separate prior experiments; (c) though IMS separates parent ions by their mobility, the fragment spectra still have the molecular peak, i.e., the information on actual parent mass is recovered. Thus, what becomes important is separating different parent ions in time, which IMS does; and (d) while using high resolution MR-TOF, in multiple cases the fragment ions from different parents could be separated into groups by their accurate masses, excluding overlaps either by elemental composition or prediction of peptide fragments in databases. Extremely rapid operation of IMS-MR-TOF tandem allows varying fragmentation energy between IMS injections, thus reconstructing fragmentation pathways or recognizing individual compounds by their prior documented fragmentation dependence on the fragmentation energy.

Reduction of Chemical Background

Time Separation of Isobars:

Ion sources like ESI, APPI, and APCI inevitably generate chemical background at a level preventing detection under generally at or between about (0.1-1) μM concentration, i.e., at 1E−4 to 1E−5 level compared to peaks of high concentrated compounds. According to author's studies, the background is formed by clusters of C, H, O and N containing compounds. Such series are well identified for m/z range under 200-300 and were extrapolated onto a higher m/z range. According to such extrapolation, mass separation of minor analyte peaks from chemical background at m/z~500-600 would require about 1 million resolution and at mz/~1000 it would require about 10 million resolution. However, the above described time separation in IMS in tandems like 61 and 71 would help separating close isobars in time, such that momentarily composition of chemical background will be much sparser and MR-TOF with R~100K would be capable of resolving minor analyte peaks from chemical background in 500-600 amu mass range. Gain in spectral sparseness may be evaluated as R/10~10 by looking at typical pattern-lines in prior art IMS experiments.

Declustering:

Referring back to FIG. 7, the CID cell 80 may be employed for soft fragmentation which will provide soft heating of parent ions such that to fragment cluster bonds (generally at or between about (0.1-0.5) eV) without breaking covalent bonds (generally at or between about (5-10) eV) of chemically stable compounds. Ion sources like Electrospray, APPI and APCI form chemical background of cluster ions. Those clusters extend to very large sizes exceeding m/z scale of conventional MS. Declustering of all ions simultaneously within ion transfer interface would not help cleaning the background, since clusters would be getting somewhat smaller but still occupying full m/z range. However, when a relatively narrow m/z range is selected within IMS and then the selected ions are subjected to declustering then covalently bound stable compounds would not shift in m/z while clusters of chemical background will, thus cleaning the spectral floor for detection of low intensive analyte compounds at trace concentrations.

Figure 8:
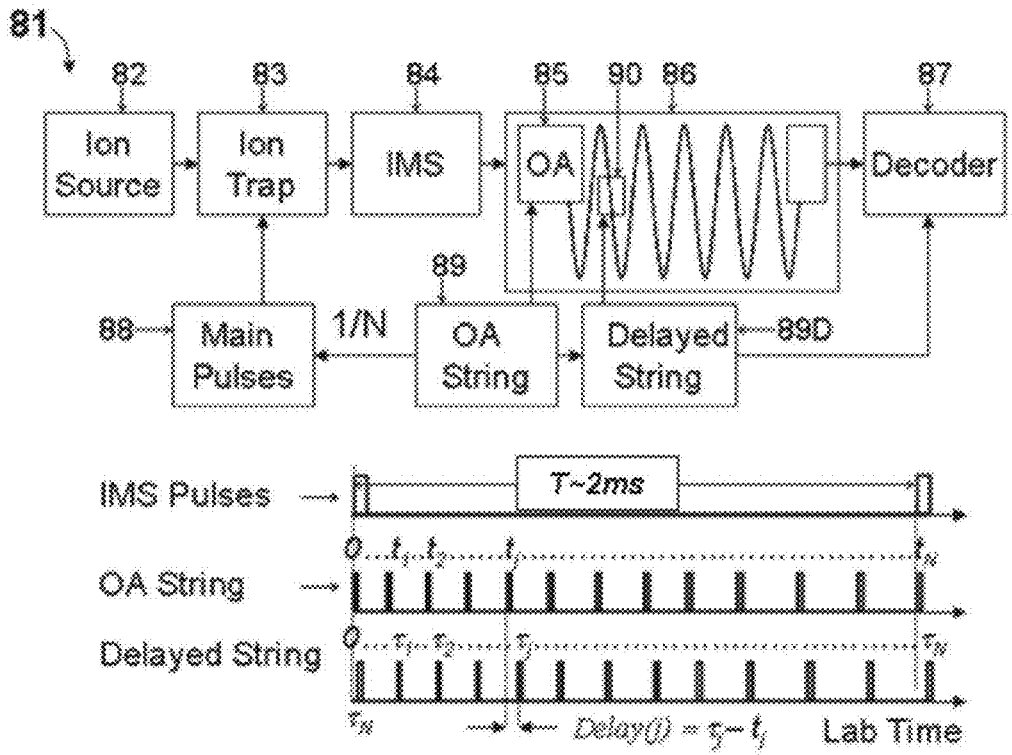
FIG. 8 shows a block scheme and time diagram for IMS-MRTOF apparatus with timed selection in the MRTOF for the correlated mobility and m/z ion selection, according to an implementation.

Correlation Gate:

In one implementation, the tandem spectrometer of the invention comprises a time selection gate within the multi-reflecting TOF for a mass-mobility correlated selection of ions. Referring to FIG. 8, another particular embodiment 81 of tandem mass spectrometer comprises an ion source 82, an ion trap 83 triggered by main pulse generator 88, an IMS 84, an OA 85 being triggered by a second encoded string generator 89, an M-TOF analyzer 86, a spectral decoder 87, and a time gate mass selector 90 in the M-TOF analyzer 86 located after one ion reflection in ion mirror, said time gate selector is triggered by a delayed string 89D. In operation, the main pulse generator 88 has period T~2 ms matching IMS separation time. The OA string generator 89 forms a string of N pulses with uneven intervals and with the total duration of the main generator $T=t_N$. The delayed string 89D is synchronized with the OA string generator 88, but has a variable delay of number j pulse $\tau_j-t_j$ which is proportional to the time $t_j$. The time selection gate 90 (e.g., a pulsed set of bipolar wires) is located after one ion cycle in the M-TOF 86 and is capable of passing through ions in the particular range of flight times, proportional to ions $(m/z)^{1/2}$. As a result, the selected ion m/z range becomes correlated with the IMS separation time $t_j$ to separate a particular class of compounds, or a particular charge state, this way reducing chemical noise in case of multi-charged analyte ions (like peptides with Electrospray ion source).

Multi-Dimensional Separations

As been mentioned above, the tandem of IMS with frequently pulsing MR-TOF allows very sensitive and highly parallel analysis at very fast time scale, also being compatible with fast separating chromatography like GC×GC and CE, or compatible with rapid surface imaging. Then the tandem becomes practically suited for higher order tandems employing yet additional separation stages which could be also called as dimensions of analytical separation. The described above methods present several examples of comprehensive analysis within multiple orthogonal analytical dimensions. 'Comprehensive' means that the analysis occurs in nested time scales (i.e., one separation does not affect timing and resolution of another separation); separates analyte in time and forms a sequentially separated analyte or ionic flow which does not cause losses of analyte or analyte ions; and occurs at maximal chromatographic speed. 'Orthogonal' means that separations do not correlate fully and provide mutually complimentary information. Multi-dimensional separation is expected to reduce interference between analyte species (initially injected as complex mixtures), to push for smaller detection limits, and to improve specificity and reliability of the identification.

As one example, FIG. 5 describes the comprehensive analysis in the following four orthogonal analytical dimensions: (i) GC1; (ii) GC2; (iii) ion mobility; and (iv) specificity of ionization by various ionization methods at switching polarity.

FIG. 6 describes the comprehensive analysis in the following five orthogonal analytical dimensions: (i) GC1; (ii) GC2; (iii) IMS; (iv) M/z; and (v) dM (see description of FIG. 6). The number of dimensions may be further increased by using multiple and rapidly switching ionization modes (vi-th dimension) and in-source fragmentation (vii-th dimension).

FIG. 7 describes example of the comprehensive analysis in the following seven orthogonal analytical dimensions: (i) GC1; (ii) GC2; (iii) IMS of parent ions; (v) m/z of parent ions (recovered in CID spectra); (vi) M/z of fragments; and (vii) dM of fragment ions. The number of dimensions can be increased by using multi-mode ionization.

In one particular method, even if not using IMS separation, the comprehensive analysis still comprises the following five orthogonal analytical dimensions: (i) GC1; (ii) GC2; (iii) M/z; and (iv) dM. The fifth analytical dimension is a multi-mode ionization.

The proposed here method of rapid IMS (non-compromising space charge capacity of ion gate and IMS) in combination with a rapid and non-compromised MR-TOF (i.e., not compromising sensitivity, resolution and speed) are expected to bring true ability of implementing those multi-dimensional separations in a practical way at time scales of conventional chromatographic separations. The proposed method of overlapped fast encoded pulsing of several tandem stages (having comparable time scales of separation) allows said multi-dimensional analysis with non-compromised performance and at high throughput and speed. Thus, the inventor proposed a set of solutions for making it practical and realized in novelty of the described methods of comprehensive analysis within multiple analytical dimensions which comprise at least four dimensions of the group: (i) gas chromatography—GC1; (ii) second and nested in time gas chromatography—GC2; (iii) multi-mode or switching polarity soft ionization like PI, CI or GD; (iv) fast switching in-source fragmentation is-CID; (v) ion mobility separation—IMS; (vi) ion fragmentation past IMS; (vii) mass spectroscopic measurements of integer mass—m/z; (viii) accurate mass measurements with extraction of mass defect and of elemental composition—dM.

3-D and 4-D AM-K-RT Tag:

Combined information on elemental composition (or at least accurate mass), on ion mobility, and on the retention time index in chromatography (LC, CE, GC or GC×GC) may serve as unique multi-dimensional tag for identification of known compounds. The identification may include the step of theoretical calculation of mobility and retention time. It is yet may be more reliable accumulating experimental databases. The same tandem may be employed for pseudo-MS-MS experiments which are expected to verify the compound by MS-MS spectra (or EI spectra in case of using EI ion source), and simultaneously measuring compounds mobility and retention index, thus filling AM-K-RT database. In subsequent analyses the database will be employed for high throughput identification of complex mixtures.

Isomers:

Isomeric information is important for sample characterization (particularly, when isomers are structural) and for determining isomer sensitive chemical reactivity. The comprehensive isomeric information has been rarely detected in mass spectrometry primarily because of low throughput and low separation capacity of employed instruments.

Figure 9:
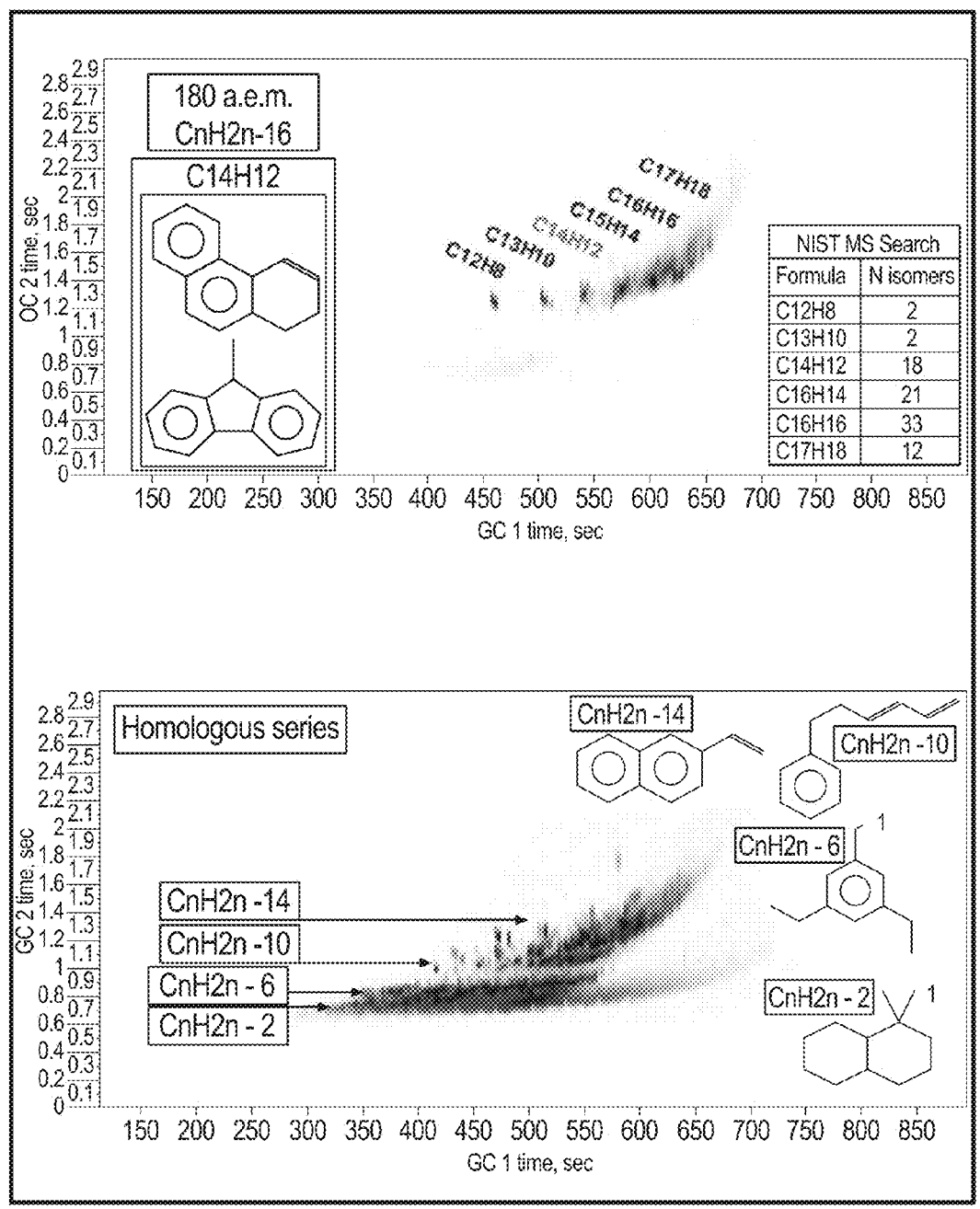
FIG. 9 shows an example of comprehensive separation of oil isomers in GC×GC-TOF with a photo-ionization source, according to an implementation.

Referring to FIG. 9, separation of isomers for diesel sample is presented with the use of GC×GC MRTOF having photo-chemical ionization. Number of spots correlates with number of isomers in NIST database. The figure shows GC×GC spots for various elemental compositions of hydrocarbons of particular homology series different by CH2 group. Still, multiple spots are not fully separated. It is expected that the additional IMS separation would increase separation capacity of the analysis.

Figure 10:
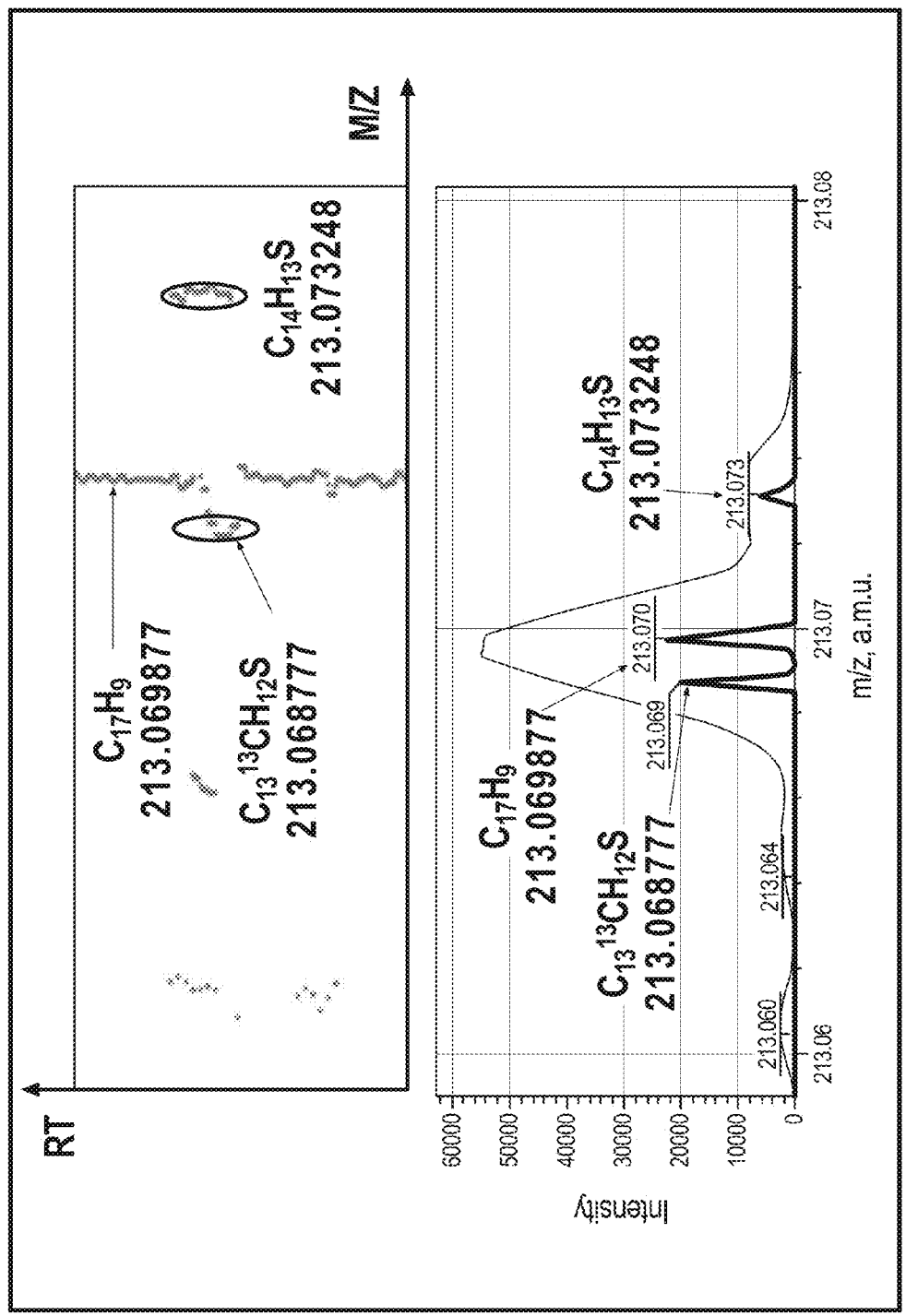
FIG. 10 shows an example of high resolution obtained due to combined GC and MS separation, where isobars are separated in time and mass resolution becomes defined by mass accuracy, according to an implementation.

Referring to FIG. 10, an example is given for a combined separation power. The same (as in FIG. 9) crude oil sample has been separated in a single GC and ionized with photo chemical ionization. Mass spectra were acquired with MR-TOF having resolution of approximately 60,000. Two isomeric compounds with 1 mDa difference were separated in time by GC as seen in the top graph plotted in axes of retention time (RT) and accurate mass (m/z). Mass peak centroids were recorded once a second and tracked with 0.1 sec time resolution. The sum of those centroid spectra composes a histogram shown in the bottom. Because of combined separation, the isobaric ions with integer mass m/z=213 and 1 mDa difference were baseline separated. This would be impossible if looking at summed profile spectra of MS alone (without GC separation) shown in the bottom graph, since peak profiles are 3 mDa wide.

Lossless FAIMS

Figure 11:
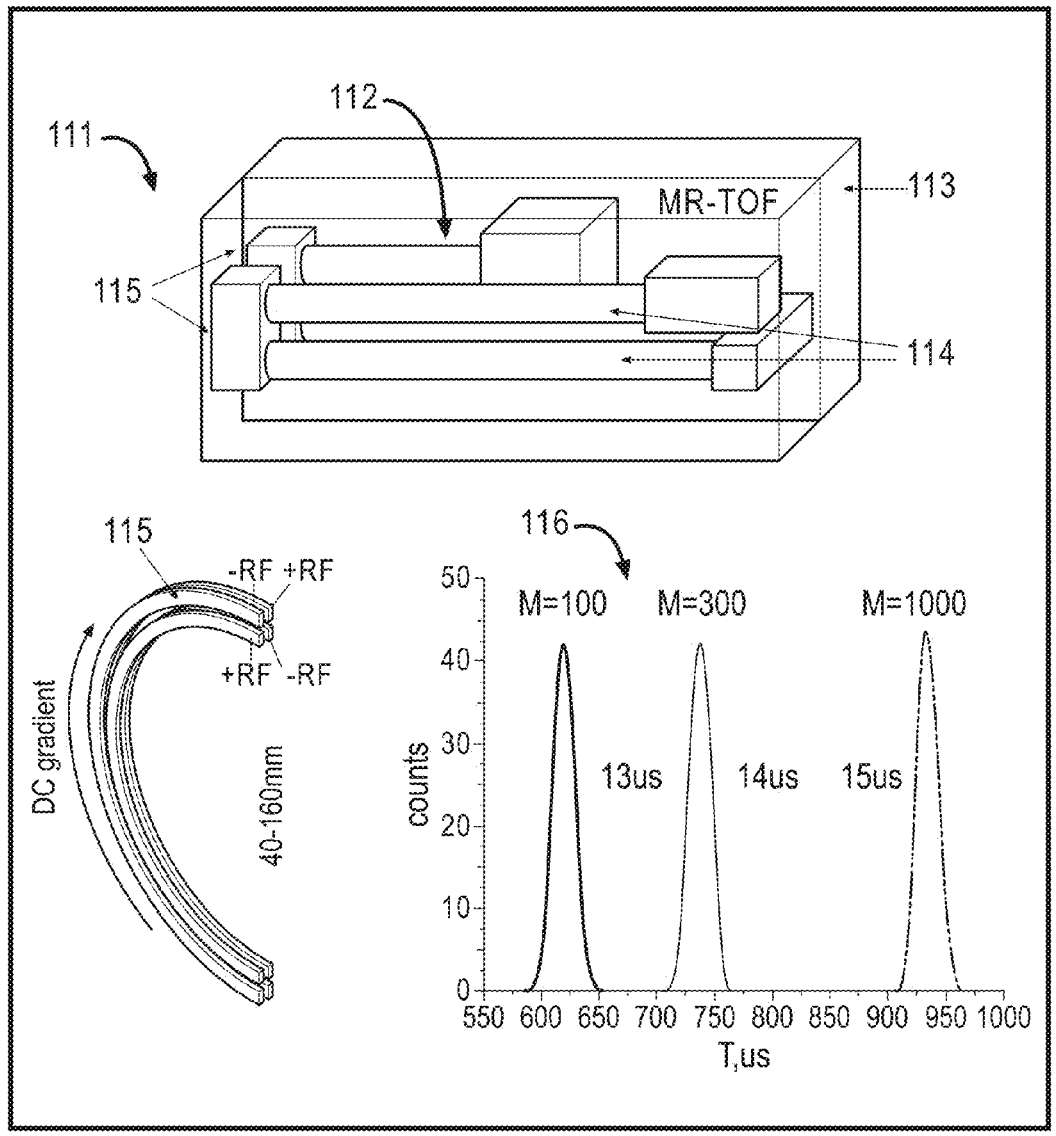
FIG. 11 shows an exemplar mobility cell arranged between coaxial cylinders with an RF retarding wall and with radial DC gradient, according to an implementation.

Referring to FIG. 11, the advantage of rapid and sensitive tandem of IMS with frequently pulsed MR-TOF allows varying of IMS-TOF settings and thus allows a practical implementation of yet another novel method of ion mobility analysis—differential ion mobility without ion losses. In prior art differential ion mobility (FAIMS), ions were separated in space, wherein one component was passed through, while other components have been rejected. The experiment took minutes to scan the FAIMS spectrum, partially due to slow FAIMS separation at atmospheric pressure and partially due to significant ion losses with the need to collect a desired ion statistics. The invention proposes combining multiple IMS experiments at different strengths of electric field such that to reveal the difference of ion mobility at strong electric field (usually corresponding to ion motion at gas dynamic velocities or faster). Preferably, the IMS cell is then filled with light gas, such as helium or nitrogen, such that fast ion motion (above gas dynamic velocity) would not cause ion fragmentation. Notably, the measurements are expected to simultaneously provide both mobility and differential mobility measurements, again without ion losses, i.e., in highly parallel fashion.

Again referring to FIG. 11, preferably, the IMS cell is extended to approximately 1-3 m length, such that to maintain at least 1 ms ion mobility time at high ion velocities (1000-3000 m/s), which is required for precise tracking of IMS profiles with frequently pulsing MR-TOF. To provide a practical solution, a novel extended IMS cell 112 is proposed. The IMS cell is folded along the MR-TOF chamber 113 and multiple straight IMS segments 114 are coupled via curved radiofrequency guides 115. Simulations shown in graph 116 confirm that curved sections do not introduce any additional time spreading originating due to RF channel curvature. Preferably, multiple curved channels could be arranged as an array of RF ion guides, such that to sustain full space charge throughput of the IMS. The novel IMS spectrometer is notably different from prior arrangements where straight and long IMS chamber (sometimes 1-2 m long) have been oriented orthogonal to the mass spectrometer chamber, thus occupying large lab area.

Figure 12:
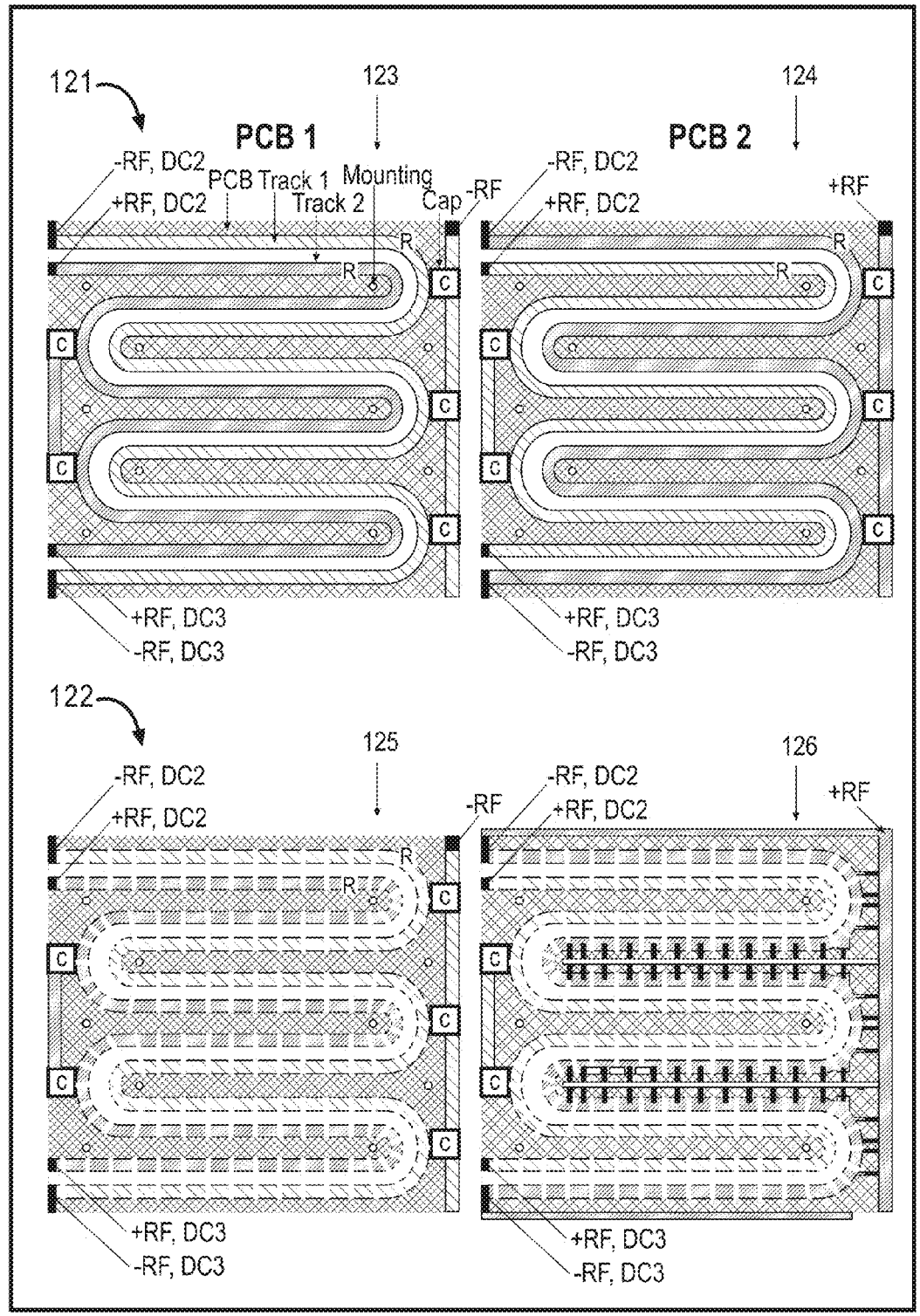
FIG. 12 shows an exemplar ion mobility cell arranged within an array of RF channels with axial DC gradient, according to an implementation.

Referring to FIG. 12, the elongated IMS cell can be arranged within two or three dimensional folded radiofrequency ion guides. The arrangement capitalizes on prior mentioned recognition of the RF delay effect. For clarity, contrary to prior art opinion, the RF fields do not spread IMS peaks in time, but rather delay ion propagation compared to other IMS areas with lower or zero RF field. Thus, RF ion guides could be constructed with no compromise on the IMS resolution. The embodiments 121 and 122 show an examples of snake folded IMS cell formed either with resistive films in the embodiment 121 or with conductive segments in the embodiment 122. The RF channel is formed with two aligned boards 123, 124 and 125,126 for two embodiments. The boards may be PC boards or boards using antistatic plastics, like Semitron. Alternatively, a segmented guide may be formed with stamped electrodes with mounting pins.

Figure 13:
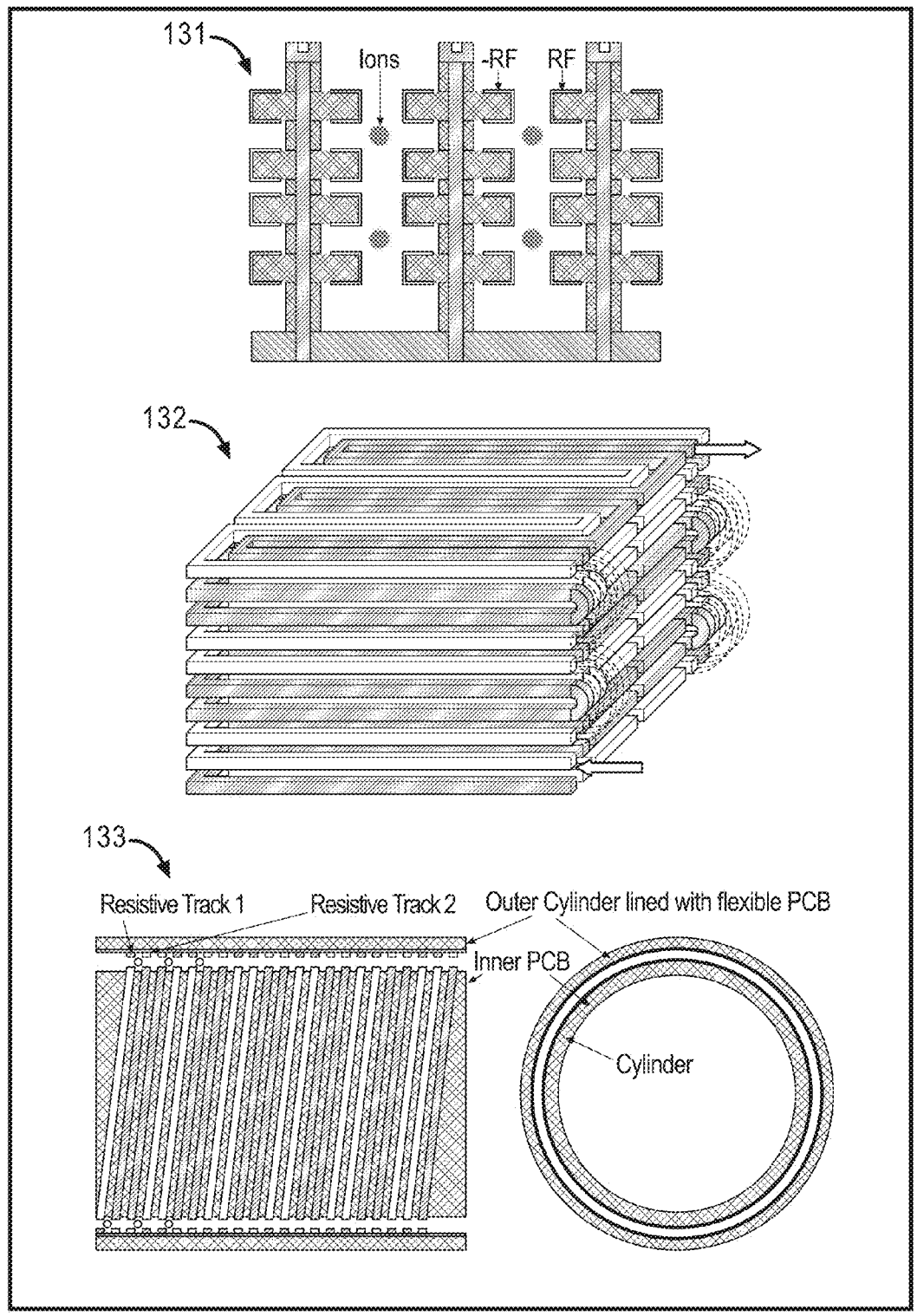
FIG. 13 shows practical examples of extending of the IMS cell length, according to an implementation.

Referring to FIG. 13, embodiments 131 and 132 show examples of 3D folded IMS, wherein different planar layers may serve either for extending the charge throughout or for extending the IMS length as in the embodiment 132. One more convenient arrangement 133 of the extended length IMS may be formed within a spiral RF channel formed with resistive strips or with conductive segments fed via resistive chain. The IMS with axial DC field and with RF radial confinement are preferably fed by RF generators with multiple secondary coils and with DC potentials fed via central taps, such that each RF phase is fed to both ends of resistive chain via at least two secondary coils and the DC signal is transmitted via secondary coils. The overall IMS electrical capacity at large IMS length becomes a practical concern. For IMS alone the gas pressure is preferably set between 1 and 10 mBar, sufficient for partial dampening of the RF motion, such that both RF frequency and amplitude could be held low (generally at or about 1 MHz and 200 Vo-p) for using practical RF generators at limited power. In case of FAIMS or combined IMS-FAIMS, the gas pressure has to be under 1 mBar and preferably under 0.1 mBar. Then the RF generators should be designed for higher power and may use ICP type of generator with powerful RF amplifiers or vacuum tubes.

Low Cost IMS-MS Tandems

The above described tandems with mobility separator do stress multiple instrumental systems: require construction of trap arrays, wide bore and large electrical capacity IMS cells, and stress dynamic range and life time of the TOF detector. Though there are visible solutions for those technical problems, the invention yet provides a low cost alternative, which is feasible for the current state of instrumentation.

Figure 14:
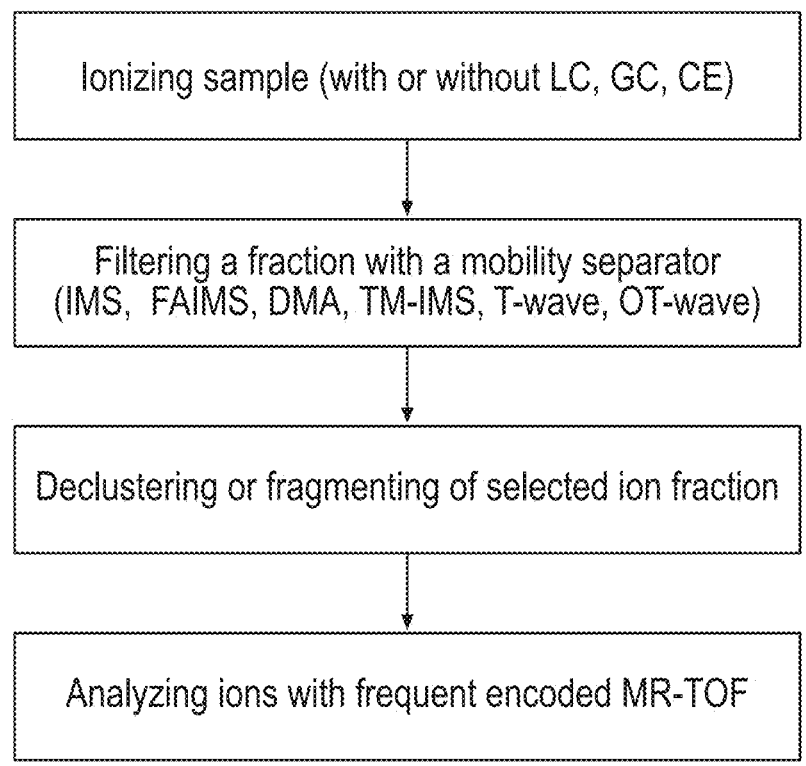
FIG. 14 shows a block diagram for method of low cost tandem mobility-mass spectrometric analysis, according to an implementation.

Referring to FIG. 14, the method of low cost tandem analysis comprises the following steps: (a) ionizing a mixture of analyte molecules in an ion source—with or without on-line chromatographic separation; (b) filtering an ion flow by either mobility or differential mobility spectrometer such that to pass through one separated ionic fraction in a time; (c) declustering or fragmenting said separated ionic fraction; and (d) analyzing said declustered or fragmented ion fraction in multi-reflecting time-of-flight mass spectrometer (MR-TOF) with encoded frequent pulsing to compensate for ionic losses at mobility filtering step.

Here is one exemplar implementation with typical numbers. A sample, such as sample for clinical analysis, e.g., for detecting hormone level, is off-line desalted and is Electrosprayed, e.g., at about 10 ul/min flow rate. The ion flow contains target analyte ions at trace amount (typically, generally at or between about (1-10) nM), plenty of matrix ions and ions of chemical noise unavoidable in ESI and known to be formed of non-covalent complexes. Direct analysis by MR-TOF with frequent encoded pulsing may be problematic for multiple reasons, wherein major reason is in strong interference between trace analyte signal, matrix, and chemical noise. The chemical noise would limit the analysis dynamic range to four orders of magnitude, even at frequent MR-TOF pulsing and R=100,000 resolution of MR-TOF. Declustering or fragmenting of the chemical noise would not help, since non-covalent complexes of chemical noise would all shift in size, but still would be occupying the entire useful mass range in MR-TOF.

The novel method suggests filtering the ion flow by any known ion mobility or differential mobility filter, such that to pass one fraction in a time, and either declustering or fragmenting the selected fraction. As an example, DMA analyzer (employing crossed DC field and gas jet for mobility filtering) known to provide mobility filtering generally at or between about 50 to 100 resolution with generally at or between a 50-100 fold duty cycle ion losses due to the filtering, and approximately 2 fold spatial ion losses. A subsequent fragmentation may be arranged either within the downstream interface (isCID) or in a CID cell. Since narrow mass range has been already selected, the chemical noise is expected to fragment and shift in m/z range compared to analyte ions. Also the spectral population is expected to be much lower (compared to unfiltered initial ion flow) which finally allows an effective application of the frequent encoded pulsing of the MR-TOF at ultimate frequency, thus dramatically saving on sensitivity and compensating for ionic losses at the mobility filtering step. At typical (generally at or about (100-300) kHz frequency of the OA operation, the signal gets improved by generally at or between about 100-300 fold, i.e., fully compensating for ion losses at mobility filtering step, while simultaneously providing accurate mass measurements (less affected by close isobars), more reliable identification supported by mobility measurement, and capability of MS-MS measurements has been described in the section "all-mass MS-MS". At the same time, there appear other analytical advantages and sensitivity savings. First, the mobility separation allows omitting standard means for interface protection with associated ion losses. Second, the sample is injected at much smaller flow rate which saves on sensitivity per injected quantity, since ESI is the concentration sensitive ion source. At smaller flow rates, the same amount of sample will provide the same intensity signal for much longer time compared to injection via LC at much higher flows. Thus, duty cycle losses of the mobility filtering do not really affect the sensitivity when comparing to LC-MS analysis.

The proposed method capitalizes on the following realizations: (a) ion losses at ion mobility filtering are compensated by high efficiency of frequent encoded pulsing within MR-TOF; (b) at the same time, the combination of mobility filtering and of ion declustering or fragmentation do dramatically improve the ratio of signal to chemical background which otherwise would be limiting efficiency of the frequent pulsing in MR-TOF; (c) ion mobility filtering allows reducing ion losses within the interface usually having means for protection against contamination which now could be eliminated along with the associated ion losses; and (d) in cases of moderate sample complexity, the upfront chromatographic separation could be replaced by the mobility separation, thus accelerating the overall analysis, making separation more reproducible and reducing sample injection flow rate to save on sample. As an example, LC can be replaced by a mobility filter and sample may be injected at 10-100 times smaller flow rate, thus extending time duration of the same intensity signal.

The method is applicable for variety of known mobility and differential mobility separators such as: (i) ion differential mobility separation in a narrow electrode gap with transverse asymmetric radiofrequency field combined with transverse adjustable DC bias (FAIMS); (ii) ion mobility separation by axial DC field in the transverse gaseous flow (DMA); (iii) ion mobility separation in a transverse modulated electrostatic field within an axial DC field and weak axial gaseous flow (TM-IMS); (iv) ion mobility separation in atmospheric or nearly atmospheric linear mobility cell with axial DC field and formation of short ion packets by Tyndal gate (IMS); (v) a travelling wave ion mobility separation (T-wave); (vi) ion mobility separation by moving segments of uniform axial field (overtone IMS); and (vii) mobility separation with axial gas jet being opposed to DC field.

The low cost and high throughput tandem of ion mobility and mass spectrometer becomes feasible for multiple ambient ionization methods such as DART, DESI, ASAP, paper spray, watermelon spray, etc. Those methods are characterized by short and convenient sample preparation and by rapid screening. However, those methods generate plenty of matrix signals and a lot of chemical noise. An improved overall separation within the low cost IMS-MR-TOF tandem is likely to be sufficient to separate and to analyze the components at high specificity and dynamic range. However, multiple conventional ionization methods would benefit, such as ESI, APCI, APPI, EI, PI/GD (described above), gaseous MALDI, etc.

Finally, if combined with liquid chromatography, the proposed low cost IMS-MR-TOF is capable of scanning the IMS stage at a speed matching LC time scale. Then two methods are visible. One is high-throughput IMS-MS analysis with ion declustering past IMS. The other is a high throughput pseudo-MS-MS, wherein mobility separated fractions are fragmented (either by isCID or within the CID cell), spectra are recorded with frequent encoded MR-TOF, fragment spectra are recovered by their correlation to the same mobility fraction and to the same retention time (RT) in LC, and finally, compounds are identified by (a) retention time; (b) mobility; (c) accurate molecular mass; and (d) fragment spectra matched to a library.

Although the present invention has been describing with reference to preferred embodiments, it will be apparent to those skilled in the art that various modifications in form and detail may be made without departing from the scope of the present invention as set forth in the accompanying claims.

What is claimed is:

1. An ion mobility spectrometer comprising:
   an ion source, said source being filled with gas at gas pressure from generally at or between about 1 mBar to 1 Bar;
   an ion gate formed of a front cap electrode, followed by a front mesh and then by a back mesh, each individual mesh defining a plurality of mesh cells, each mesh cell having a mesh cell size between 0.1-1 mm, wherein the meshes are generally parallel with one another and spaced at a distance substantially equal to the mesh cell size;
   a radiofrequency (RF) generator connected between the meshes;
   a direct current (DC) generator configured to apply a switching or adjustable DC signal to the cap electrode and meshes;
   wherein the RF and DC generators are configured to form a local RF field between the front mesh and the back mesh while attracting ions toward the RF field region by a DC field which is sufficiently small to prevent ion penetration through the barrier of the RF field to thereby yield ion localization in local RF traps around mesh cells;
   an ion drift space filled with gas at pressure from generally at or between about (1 to 30) mBar; and
   an ion detector.

2. An apparatus as set forth in claim 1, wherein an axis of the ion source is oriented substantially parallel to said meshes.

3. An apparatus as set forth in claim 1, further comprising an RF ion guide between the ion source and the ion gate, and wherein the RF ion guide is selected from the group consisting of: (i) an ion funnel; (ii) an RF channel; and (iii) a multipole ion guide with axial field.

4. An apparatus as set forth in claim 1, wherein the source has fragmentation means and means for switching said fragmentation at a time scale of chromatographic separation.

5. An apparatus as set forth in claim 1, further comprising: two coaxial set of electrodes, outer and inner, wherein within each of the inner and outer sets of electrodes, said electrodes are connected via a resistive chain adapted to provide axial DC gradient within at least one of said sets of electrodes, and wherein said sets of electrodes are connected to alternated radio-frequency supply for radial ion repulsion such that DC potential distribution between said two sets may be biased to provide radial DC field thereby pushing ions against an RF barrier.

6. An apparatus as set forth in claim 1, further comprising: an array of radiofrequency ion guides with a distributed axial DC field, having a spatial arrangement selected from the group consisting of: a two dimensional planar array, a coaxially wrapped two dimensional array, and a three-dimensional array comprising multiple planar layers.

7. A method of ion mobility spectrometric analysis, comprising the following steps:
generating ions within an ion source operating at gas pressure from generally at or between about 1 mBar to 1 Bar;
introducing ions into an ion gate formed of a front cap electrode, followed by a front mesh spaced parallel to a back mesh, each individual mesh defining a plurality of mesh cells, each mesh cell having a mesh cell size between 0.1-1 mm;
forming a local RF field between the front and back meshes while attracting ions toward the RF field region by a DC field which is sufficiently small to prevent ion penetration through the barrier of the RF field to thereby yield ion localization in local RF traps around mesh cells;
propelling ions through the RF field by a pulsed switch of a DC field generally in the region of the RF field to thereby yield short ion packets;
separating ions by mobility characteristic within an electrostatic field at gas pressure from generally at or between about (1 to 30) mBar;
detecting a time dependent signal on a detector; and
wherein the front mesh is spaced from the back mesh at a distance substantially equal to the mesh cell size.

8. A method as set forth in claim 7, further comprising a step of analyte separation by a step selected from the group consisting of: (i) a method of gas chromatographic separation; (ii) a method of dual stage gas chromatographic separation; (iii) liquid chromatography; and (iv) capillary electrophoresis.

9. A method as set forth in claim 7, wherein said step of ionization is selected from the group consisting of: (i) a photoionization; (ii) a photo-chemical ionization with a dopant; (iii) a chemical ionization with proton transfer reactions; (iv) a chemical ionization with electron attachment ionization; (v) analyte ionization by conditioned products of a glow discharge; (vi) an Electrospray ionization; (vii) an atmospheric pressure photo-chemical ionization; (viii) an atmospheric pressure chemical ionization; and (ix) matrix assisted laser desorption.

10. A method as set forth in claim 7, further comprising step of switching one of the group: (i) between ionization methods; (ii) ion polarities; (iii) between fragmentation and soft ion transfer; and (iv) between states of fragmentation.

11. A tandem ion mobility mass-spectrometer comprising:
a gaseous ion source;
one of (i) a dual mesh gate IMS RF gate connected to an RF signal and (ii) a ring shaped ion trap for trapping and pulsed transfer of ions at gas pressure from generally at or between about (1 to 100) mBar;
an ion mobility drift space past said one of (i) said dual mesh IMS RF gate and (ii) said ring shaped ion trap;
a multi-reflecting time-of-flight mass spectrometer with an orthogonal accelerator;
a signal generator providing a pulse string composed of frequent start signals with encoded uneven intervals for triggering both (A) said one of (i) said dual mesh IMS RF gate and (ii) said ring shaped ion trap at mean frequency at or above 1 kHz and (B) said orthogonal accelerator at mean frequency at or above 100 kHz, wherein the pulse string duration is comparable to IMS separation time; and
a data system with acquisition period matching the duration of said pulse strings and also providing IMS-MS spectral decoding with the account of the coded pulse intervals and of intensity distributions within signal series.

12. An apparatus as set forth in claim 11, further comprising one tapered exit IMS section selected from the group consisting of: (i) an ion funnel; (ii) an ion funnel with a central expanding and contracting sections; (iii) a multipole set formed of multipole PCB sections; and (iv) a converging ion funnel further comprising at least one electrode on axis for radial repulsion with DC field.

13. A method of rapid tandem IMS-TOF analysis comprising the following steps:
accumulating ions by utilizing a RF field in-front of a dual mesh or inside a ring shaped ion trapping region with RF ion confinement;
ejecting ions utilizing a pulsed or mass dependent ion ejection by a repetitive pulse string with uneven intervals and at mean frequency at or above approximately 1 kHz;
subsequent ion mobility separation at gas pressure from generally at or between about (1 to 100) mBar;
spatial focusing of ion flow past said step of ion mobility separation;
a pulsed orthogonal ion acceleration encoded by a repetitive pulse string with uneven intervals and at mean frequency at or above approximately 100 kHz;
time-of-flight analysis within a multi-reflecting electrostatic fields; and
decoding information on ion mobility time, ion mass and ion intensity with the account of the encoded and uneven pulse intervals and on intensity distribution within signal series corresponding to same m/z specie.

14. A method as set forth in claim 13, wherein said step of spectral decoding employs a multi-dimensional algorithm for analyzing data clusters in a multi-dimensional space of chromatographic time, ion mobility time and flight time in MR-TOF for accounting for all ion signals of any particular m/z specie during its chromatographic and ion mobility peaks while analyzing separation time profiles.

15. A method as set forth in claim 13, further comprising:
performing either ion fragmentation or ion declustering (soft fragmentation) between steps of ion mobility separation and of time-of-flight analysis.

16. A method as set forth in claim 13, further comprising: deconvoluting the signal for accurate assignment of mobility time and for time correlation between product ions.

17. A method as set forth in claim 13, further comprising: measuring centroids of mass spectral peaks in elementary spectra and converting profile data into stick spectra.

18. A method as set forth in claim 16, further comprising: recording detector signal in a data logging format with the stamp of laboratory time prior to steps of deconvolution and decoding.

19. A method as set forth in claim 13, further comprising: transmitting ions within a defined time window and at a defined spatial position of one ion reflection within said multi-reflecting electrostatic fields, and wherein said defined time window is adjusted with currently transmitted mobility time for mobility to yield a mass correlated ion selection.

20. A method as set forth in claim 13, further comprising a step of ion m/z sequence inversion at a slow ramping of DC field propelling ions through said RF barrier at said gating step.

21. An apparatus as set forth in claim 1, wherein each individual mesh is composed of a grid of wires, and wherein the mesh cell size is defined by a space between the wires.

22. A method as set forth in claim 7, wherein each individual mesh is composed of a grid of wires, and wherein the mesh cell size is defined by a space between the wires.

* * * * *